US012558407B2

(12) United States Patent
Sayour et al.

(10) Patent No.: US 12,558,407 B2
(45) Date of Patent: Feb. 24, 2026

(54) COMPOSITIONS FOR TREATMENT OF DIFFUSE INTRINSIC PONTINE GLIOMA

(71) Applicant: University of Florida Research Foundation, Inc., Gainesville, FL (US)

(72) Inventors: Elias Sayour, Newberry, FL (US); James Andrew McGuiness, Gainesville, FL (US); Hector Ruben Mendez-Gomez, Gainesville, FL (US); Duane A. Mitchell, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 1089 days.

(21) Appl. No.: 17/607,495

(22) PCT Filed: May 1, 2020

(86) PCT No.: PCT/US2020/031096
§ 371 (c)(1),
(2) Date: Oct. 29, 2021

(87) PCT Pub. No.: WO2020/242720
PCT Pub. Date: Dec. 3, 2020

(65) Prior Publication Data

US 2022/0218808 A1 Jul. 14, 2022

Related U.S. Application Data

(60) Provisional application No. 62/842,525, filed on May 2, 2019.

(51) Int. Cl.

| | |
|---|---|
| ***A61K 39/00*** | (2006.01) |
| ***A61P 35/00*** | (2006.01) |
| ***C07K 14/705*** | (2006.01) |
| ***C07K 14/74*** | (2006.01) |

(52) U.S. Cl.
CPC ... *A61K 39/001114* (2018.08); *A61K 39/0011* (2013.01); *A61P 35/00* (2018.01); *C07K 14/70539* (2013.01); *C07K 14/70596* (2013.01); *A61K 2039/53* (2013.01); *A61K 2039/55555* (2013.01); *A61K 2039/80* (2018.08); *C07K 2319/00* (2013.01)

(58) Field of Classification Search
CPC ...... A61K 2039/53; A61K 2039/55555; A61K 2039/80; A61K 39/0011; A61K 39/001114; A61P 35/00; C07K 14/70539; C07K 14/70596; C07K 2319/00; C07K 14/4748
See application file for complete search history.

(56) References Cited

U.S. PATENT DOCUMENTS

| | | | | |
|---|---|---|---|---|
| 4,342,776 | A | 8/1982 | Cragoe et al. | |
| 4,399,276 | A | 8/1983 | Miyasaka et al. | |
| 4,473,692 | A | 9/1984 | Miyasaka et al. | |
| 4,513,138 | A | 4/1985 | Miyasaka et al. | |
| 4,526,988 | A | 7/1985 | Hertel | |
| 4,545,880 | A | 10/1985 | Miyasaka et al. | |
| 4,604,463 | A | 8/1986 | Miyasaka et al. | |
| 4,808,614 | A | 2/1989 | Hertel | |
| 5,004,758 | A | 4/1991 | Boehm et al. | |
| 5,223,608 | A | 6/1993 | Chou et al. | |
| 5,620,985 | A | 4/1997 | Jacquesy et al. | |
| 6,630,124 | B1 | 10/2003 | Gozes et al. | |
| 2010/0324120 | A1 | 12/2010 | Chen et al. | |
| 2012/0178702 | A1 | 7/2012 | Huang et al. | |
| 2013/0059360 | A1 | 3/2013 | Bossard et al. | |
| 2013/0072709 | A1 | 3/2013 | Mcmanus et al. | |
| 2013/0090372 | A1 | 4/2013 | Budzik et al. | |
| 2013/0115299 | A1 | 5/2013 | Chiou et al. | |
| 2013/0150625 | A1 | 6/2013 | Budzik et al. | |
| 2013/0196948 | A1 | 8/2013 | Fisher et al. | |
| 2015/0182627 | A1 | 7/2015 | Park et al. | |
| 2017/0281742 | A1 | 10/2017 | Okada et al. | |
| 2017/0367982 | A1 | 12/2017 | Nandwana et al. | |
| 2018/0155403 | A1* | 6/2018 | Platten | A61P 35/00 |

FOREIGN PATENT DOCUMENTS

| | | | |
|---|---|---|---|
| EP | 0056692 | A1 | 7/1982 |
| EP | 0074256 | A1 | 3/1983 |
| EP | 0074770 | A1 | 3/1983 |

(Continued)

OTHER PUBLICATIONS

Reto A Schwendener Ther Adv Vaccines, Nov. 2014, 2(6): pp. 159-182.*
Ragelle et al., Nanoparticle-based drug delivery systems: a commercial and regulatory outlook as the field matures, Expert Opin. Drug Deliv., 14(7):851-864 (2017).
Ransohoff et al., Three or more routes for leukocyte migration into the central nervous system, Nature Reviews Immunology, 3(7):569-81 (2003).

(Continued)

*Primary Examiner* — Bao Q Li
(74) *Attorney, Agent, or Firm* — MARSHALL, GERSTEIN & BORUN LLP

(57) ABSTRACT

Provided herein are compositions comprising a liposome comprising RNA molecules and a cationic lipid, wherein the RNA molecules encode at least one MHC Class II epitope of a mutant Histone 3 (H3) protein comprising a K27M mutation and optionally at least one MHC Class I epitope of the mutant H3 protein. In exemplary embodiments, the RNA molecules comprise a sequence of SEQ ID NO: 12 or 14. Methods of increasing central memory T cells, increasing an immune response, or treating a diffuse midline glioma (DMG), in a subject are provided herein. In exemplary embodiments, the methods comprise administering to the subject the compositions provided herein.

18 Claims, 5 Drawing Sheets

Specification includes a Sequence Listing.

(56) References Cited

FOREIGN PATENT DOCUMENTS

| | | | | |
|---|---|---|---|---|
| EP | 0088642 | A2 | 9/1983 | |
| EP | 0137145 | A1 | 4/1985 | |
| EP | 0184365 | A2 | 6/1986 | |
| EP | 0321122 | A2 | 6/1989 | |
| EP | 0418099 | A2 | 3/1991 | |
| EP | 2711000 | A1 | 3/2014 | |
| WO | 2007/047981 | A2 | 4/2007 | |
| WO | 2011/112597 | A1 | 9/2011 | |
| WO | 2012/099755 | A1 | 7/2012 | |
| WO | 2012/131104 | A2 | 10/2012 | |
| WO | 2012/131106 | A1 | 10/2012 | |
| WO | 2012/170930 | A1 | 12/2012 | |
| WO | 2013/033438 | A2 | 3/2013 | |
| WO | WO-2013075237 | A1 * | 5/2013 | A61P 35/00 |
| WO | 2013/105101 | A1 | 7/2013 | |
| WO | 2013/143555 | A1 | 10/2013 | |
| WO | 2014/057432 | A2 | 4/2014 | |
| WO | 2014/127917 | A1 | 8/2014 | |
| WO | 2014/165103 | A1 | 10/2014 | |
| WO | 2015/198326 | A1 | 12/2015 | |
| WO | 2017/099829 | A1 | 6/2017 | |
| WO | 2018/078053 | A1 | 5/2018 | |
| WO | 2018/144082 | A1 | 8/2018 | |
| WO | 2019/217593 | A1 | 11/2019 | |

OTHER PUBLICATIONS

Rapp et al., Identification of T cell target antigens in glioblastoma stem-like cells using an integrated proteomics-based approach in patient specimens, Acta. Neuropathol., 134(2):297-316 (2017).
Rhodes et al., ONCOMINE: a cancer microarray database and integrated data-mining platform, Neoplasia., 6(1):1-6 (2004).
Ribas, Anti-CTLA4 Antibody Clinical Trials in Melanoma, Update Cancer Ther., 2(3):133-9 (2007).
Roesch et al., A temporarily distinct subpopulation of slow-cycling melanoma cells is required for continuous tumor growth, Cell, 141(4):583-94 (2010).
Roesch et al., Overcoming intrinsic multidrug resistance in melanoma by blocking the mitochondrial respiratory chain of slow-cycling JARID1B(high) cells, Cancer Cell, 23(6):811-25 (2013).
Rosa et al., A radial glia gene marker, fatty acid binding protein 7 (FABP7), is involved in proliferation and invasion of glioblastoma cells, PLoS One, 7(12):e52113 (2012).
Rosenberg et al., Cancer regression in patients with metastatic melanoma after the transfer of autologous antitumor lymphocytes, Proceedings of the National Academy of Sciences of the United States of America, 101(Suppl 2):14639-14645 (2004).
Rosenberg et al., Durable complete responses in heavily pretreated patients with metastatic melanoma using T-cell transfer immunotherapy, Clin. Cancer Res., 17:4550-4557 (2011).
Rosenberg, Raising the bar: the curative potential of human cancer immunotherapy, Science Translational Medicine, 4(127):127ps8 (2012).
Salazar-Ramiro et al., Role of Redox Status in Development of Glioblastoma, Front. Immunol., 7:156 (2016).
Sampson et al., Greater chemotherapy-induced lymphopenia enhances tumor-specific immune responses that eliminate EGFRvIII-expressing tumor cells in patients with glioblastoma, Neuro. Oncol., 13(3):324-33 (2011).
Sampson et al., Immunologic escape after prolonged progression-free survival with epidermal growth factor receptor variant III peptide vaccination in patients with newly diagnosed glioblastoma, J. Clin. Oncol., 28(31):4722-9 (2010).
Sanchez-Perez et al., Myeloablative temozolomide enhances CD8? T-cell responses to vaccine and is required for efficacy against brain tumors in mice, PloS one, 8(3):e59082 (2013).
Sarkisian et al., Detection of primary cilia in human glioblastoma, J. Neurooncol., 117(1):15-24 (2014).
Sayour et al., Cancer Vaccine Immunotherapy with RNA-Loaded Liposomes, Int. J. Mol. Sci., 19(10):2890 (2018).
Sayour et al., Immunotherapy for Pediatric Brain Tumors, Brain Sci., 7(10):137 (2017).
Sayour et al., Personalized Tumor RNA Loaded Lipid-Nanoparticles Prime the Systemic and Intratumoral Milieu for Response to Cancer Immunotherapy, Nano Lett., 18(10):6195-6206 (2018).
Sayour et al., Systemic activation of antigen-presenting cells via RNA-loaded nanoparticles, Oncoimmunology, 6(1):e1256527 (2017).
Sayour, E., et al., "IMMU-08. Unlocking Cancer Immunotherapy Against Pediatric Brain Tumors With Transcriptome Loaded Nanoparticles," Neuro-Oncology, 21(Supplement 2):1194(2019).
Schadendorf et al., Pooled Analysis of Long-Term Survival Data From Phase II and Phase III Trials of Ipilimumab in Unresectable or Metastatic Melanoma, J. Clin. Oncol., 33(17):1889-1894 (2015).
Scheetz et al., Engineering patient-specific cancer immunotherapies, Nat. Bio. Eng., 3(10):768-782 (2019).
Scherer et al., Magnetofection: enhancing and targeting gene delivery by magnetic force in vitro and in vivo, Gene. Ther., 9(2):102-109 (2002).
Schumacher et al., Neoantigens in cancer immunotherapy, Science, 348:69-74 (2015).
Schuster et al., Vaccination with patient-specific tumor-derived antigen in first remission improves disease-free survival in follicular lymphoma, J. Clin. Oncol., 29(20):2787-94 (2011).
Schwake, M., et al., "Lysosomal membrane proteins and their central role in physiology," Traffic, 14(7):739-748(2013).
Semple et al., Rational design of cationic lipids for siRNA delivery, Nat. Biotechnol., 28(2):172-176 (2010).
Sharp, RNA interference-2001, Genes Dev., 15(5):485-490 (2001).
Shen et al., Cloned dendritic cells can present exogenous antigens on both MHC class I and class II molecules, J. Immunol., 158(6):2723-2730 (1997).
Shi et al., Cancer nanomedicine: progress, challenges and opportunities, Nat. Rev. Cancer, 17(1):20-37 (2017).
Shimamoto et al., Peptibodies: A flexible alternative format to antibodies, mAbs, 4(5):586-591 (2012).
Shimono et al., Downregulation of miRNA-200c links breast cancer stem cells with normal stem cells, Cell, 138(3):592-603 (2009).
Shoshan-Barmatz et al., The voltage-dependent anion channel: characterization, modulation, and role in mitochondrial function in cell life and death, Cell Biochem. Biophys., 39(3):279-92 (2003).
Siebzehnrubl et al., Isolation and characterization of adult neural stem cell, Methods Mol. Biol., 750:61-77 (2011).
Siebzehnrubl et al., The ZEB1 pathway links glioblastoma initiation, invasion and chemoresistance, EMBO Mol. Med., 5(8):1196-1212 (2013).
Singh et al., Autophagy regulates lipid metabolism, Nature, 458(7242):1131-5 (2009).
Singh et al., EMT, cancer stem cells and drug resistance: an emerging axis of evil in the war on cancer, Oncogene, 29(34):4741-51 (2010).
Singh et al., Oncogenes Activate an Autonomous Transcriptional Regulatory Circuit That Drives Glioblastoma, Cell reports, 18(4):961-976 (2017).
Soema et al., Predicting the influence of liposomal lipid composition on liposome size, zeta potential and liposome-induced dendritic cell maturation using a design of experiments approach, Eur. J. Pharm. Biopharm., 94:427-435 (2015).
Sonabend et al., Medulloblasoma: challenges for effective immunotherapy, Journal of neurooncology, 108(1):1-10 (2012).
Spiess et al., Alternative molecular formats and therapeutic applications for bispecific antibodies, Molecular Immunology, 67(2 Part A):95-106 (2015).
Srinivas et al., Imaging of cellular therapies, Adv. Drug Deliv. Rev., 62(11):1080-1093 (2010).
Stoll et al., Neural Stem Cells in the Adult Subventricular Zone Oxidize Fatty Acids to Produce Energy and Support Neurogenic Activity, Stem Cells, 33(7):2306-19 (2015).
Strobel et al., Human dendritic cells transfected with either RNA or DNA encoding influenza matrix protein M1 differ in their ability to stimulate cytotoxic T lymphocytes, Gene therapy, 7(23):2028-35 (2000).

(56) References Cited

OTHER PUBLICATIONS

Stupp et al., Effects of radiotherapy with concomitant and adjuvant temozolomide versus radiotherapy alone on survival in glioblastoma in a randomised phase III study: 5-year analysis of the EORTC-NCIC trial, The Lancet Oncology, 10(5):459-66 (2009).
Stupp et al., Maintenance Therapy With Tumor-Treating Fields Plus Temozolomide vs Temozolomide Alone for Glioblastoma: A Randomized Clinical Trial, JAMA, 314(23):2535-43 (2015).
Stupp et al., Radiotherapy plus concomitant and adjuvant temozolomide for glioblastoma, N. Engl. J. Med., 352(10):987-96 (2005).
Sun et al., Immunotherapy using slow-cycling tumor cells prolonged overall survival of tumor-bearing mice, BMC Med., 10(27):172 (2012).
Szklarczyk et al., STRING v10: protein-protein interaction networks, integrated over the tree of life, Nucleic Acids Res., 43:D447-52 (2015).
Tang et al., PD-L1 on host cells is essential for PD-L1 blockade-mediated tumor regression, The Journal of Clinical Investigation, 128(2):580-588 (2018).
Tellingen et al., Pharmacology, bio-analysis and pharmacokinetics of the vinca alkaloids and semi-synthetic derivatives (review), Anticancer Research, 12(5):1699-1716 (1992).
Tendeloo et al., Highly efficient gene delivery by mRNA electroporation in human hematopoietic cells: superiority to lipofection and passive pulsing of mRNA and to electroporation of plasmid cDNA for tumor antigen loading of dendritic cells, Blood, 98(1):49-56 (2001).
Tirinato et al., Lipid droplets: a new player in colorectal cancer stem cells unveiled by spectroscopic imaging, Stem. Cells, 33(1):35-44 (2015).
Tirosh et al., Dissecting the multicellular ecosystem of metastatic melanoma by single-cell RNA-seq, Science, 352:189-96 (2016).
Tirosh et al., Single-cell RNA-seq supports a developmental hierarchy in human oligodendroglioma, Nature, 539:309-313 (2016).
Uhlen et al., Proteomics. Tissue-based map of the human proteome, Science, 347:1260419 (2015).
Ui-Tei et al., Sensitive assay of RNA interference in drosophila and chinese hamster cultured cells using firefly luciferase gene as target, FEBS Lett., 479(3):79-82 (2000).
Vanner et al., Quiescent sox2(+) cells drive hierarchical growth and relapse in sonic hedgehog subgroup medulloblastoma, Cancer Cell, 26(1):33-47 (2014).
Velazquez et al., Autophagy regulation depends on ER homeostasis controlled by lipid droplets, Autophagy, 12(8):1409-10 (2016).
Venteicher et al., Decoupling genetics, lineages, and microenvironment in IDH-mutant gliomas by single-cell RNA-seq, Science, 355:eaai8478 (2017).
Verdijk et al., Sensitivity of magnetic resonance imaging of dendritic cells for in vivo tracking of cellular cancer vaccines, Int. J. Cancer, 120(5):978-984 (2007).
Viale et al., Oncogene ablation-resistant pancreatic cancer cells depend on mitochondrial function, Nature, 514(7524):628-32 (2014).
Vlashi et al., Metabolic state of glioma stem cells and nontumorigenic cells, Proc. Natl. Acad. Sci. USA, 108(38):16062-7 (2011).
Vries et al., Magnetic resonance tracking of dendritic cells in melanoma patients for monitoring of cellular therapy, Nat. Biotechnol., 23(11):1407-1413 (2005).
Wang et al., Iron Drives T Helper Cell Pathogenicity by Promoting RNA-Binding Protein PCBP1-Mediated Proinflammatory Cytokine Production, Immunity 49(1):80-92e7 (2018).
Wani et al., Plant antitumor agents. 18. synthesis and biological activity of camptothecin analogues, J. Med. Chem., 23(5):554-560 (1980).
Wani et al., Plant antitumor agents. 23. Synthesis and antileukemic activity of camptothecin analogues, J. Med. Chem., 29(11):2358-2363 (1986).
Wani et al., Plant antitumor agents. 25. total synthesis and antileukemic activity of ring a substituted camptothecin analogues. structure-activity correlations, J. Med. Chem., 30(10):1774-1779 (1987).
Wei et al., Fundamental mechanisms of immune checkpoint blockade therapy, Cancer Discovery, 8(9):1069-1086 (2018).
Weller et al., Rindopepimut with temozolomide for patients with newly diagnosed, EGFRvIII-expressing glioblastoma (Act IV): a randomised, double-blind, international phase 3 trial, The Lancet Oncology, 18(10):1373-1385 (2017).
Weller et al., Rindopepimut with temozolomide for patients with newly diagnosed, EGFRvIII-expressing glioblastoma (Act IV): a randomised, double-blind, international phase 3 trial, The Lancet Oncology, 18(10):1373-85 (2017).
Wellner et al., The EMT-activator ZEB1 promotes tumorigenicity by repressing stemness-inhibiting microRNAs, Nat. Cell Biol., 11(12):1487-95 (2009).
White et al., Autophagy, Metabolism, and Cancer, Clin. Cancer Res., 21(22):5037-46 (2015).
Wilgenhof et al., Phase II Study of Autologous Monocyte-Derived mRNA Electroporated Dendritic Cells (TriMixDC-MEL) Plus Ipilimumab in Patients With Pretreated Advanced Melanoma, J. Clin. Oncol., 34(12):1330-1338 (2016).
Wong et al., Module map of stem cell genes guides creation of epithelial cancer stem cells, Cell Stem. Cell., 2(4):333-44 (2008).
Yan et al., Nature versus Nurture in Determining Athletic Ability, Med. Sport Sci., 61:15-28 (2016).
Zamore et al., RNAi: double-stranded RNA directs the ATP-dependent cleavage of mRNA at 21 to 23 nucleotide intervals, Cell, 101(1):25-33 (2000).
Zanganeh et al., Iron oxide nanoparticles inhibit tumour growth by inducing pro-inflammatory macrophage polarization in tumour tissues, Nat. Nanotechnol., 11(11):986-994 (2016).
Zaretsky et al., Mutations associated with acquired resistance to pd-1 blockade in melanoma, The New England journal of medicine, 375(9):819-829 (2016).
Zeuner et al., Elimination of quiescent/slow-proliferating cancer stem cells by Bcl-XL inhibition in non-small cell lung cancer, Cell Death Differ, 21(12):1877-88 (2014).
Zhang et al., Antigen-loaded dendritic cell migration: MR imaging in a pancreatic carcinoma model, Radiology, 274:192-200 (2015).
Zhou et al., Predicting human tumor drug concentrations from a preclinical pharmacokinetic model of temozolomide brain disposition, Clin. Cancer Res., 13(14):4271-9 (2013).
Zitvogel et al., Cancer despite immunosurveillance: immunoselection and immunosubversion, Nature Reviews Immunology, 6(10):715-727 (2006).
Aarntzen et al., Vaccination with mRNA-electroporated dendritic cells induces robust tumor antigen-specific CD4+ and CD8+ T cells responses in stage III and IV melanoma patients, Clin. Cancer Res., 18(19):5460-5470 (2012).
Abbott et al., Astrocyte-endothelial interactions at the blood-brain barrier, Nat. Rev. Neurosci., 7(1):41-53 (2006).
Ahrens et al., Tracking immune cells in vivo using magnetic resonance imaging, Nat. Rev. Immunol., 13(10):755-763 (2013).
Aigner et al., The transcription factor ZEB1 (deltaEF1) promotes tumour cell dedifferentiation by repressing master regulators of epithelial polarity, Oncogene, 26(49):6979-88 (2007).
Anguille et al., Dendritic cell vaccination as postremission treatment to prevent or delay relapse in acute myeloid leukemia, Blood, 130(5):1713-1721 (2017).
Ansell et al., PD-1 blockade with nivolumab in relapsed or refractory Hodgkin's lymphoma, The New England Journal of Medicine, 372(4):311-319 (2015).
Anselmo et al., Nanoparticles in the clinic, Bioeng. Transl. Med., 1(1):10-29 (2016).
Bader et al., The therapeutic potential of microRNAs, Innovations in Pharmaceutical Technology, 52-55 (2011).
Badoual et al., PD-1-expressing tumor-infiltrating T cells are a favorable prognostic biomarker in HPV-associated head and neck cancer, Cancer Research, 73(1):128-138 (2013).
Batich et al., Long-term Survival in Glioblastoma with Cytomegalovirus pp65-Targeted Vaccination, Clin. Cancer Res., 23(8):1898-1909 (2017).
Beloribi-Djefaflia et al., Lipid metabolic reprogramming in cancer cells, Oncogenesis, 5(1):e189 (2016).

(56) References Cited

OTHER PUBLICATIONS

Belounis et al., Autophagy is associated with chemoresistance in neuroblastoma, BMC Cancer, 16(1):891 (2016).
Bensaad et al., Fatty acid uptake and lipid storage induced by HIF-1a contribute to cell growth and survival after hypoxia-reoxygenation, Cell Reports 9(1):349-65 (2014).
Bernstein et al., Role for a bidentate ribonuclease in the initiation step of RNA interference, Nature, 409:363-366 (2001).
Blachly-Dyson et al., VDAC channels, IUBMB life, 52:113-8 (2001).
Blasius et al., Intracellular toll-like receptors, Immunity, 32(3):305-315 (2010).
Bloch et al., Gliomas promote immunosuppression through induction of B7—H1 expression in tumor-associated macrophages, Clinical Cancer Research, 19(12):3165-3175 (2013).
Bol et al., Intranodal vaccination with mRNA-optimized dendritic cells in metastatic melanoma patients, Oncoimmunology, 4(8):e1019197 (2015).
Borghaei et al., Nivolumab versus docetaxel in advanced nonsquamous non-small-cell lung cancer, The New England Journal of Medicine, 373(17):1627-1639 (2015).
Brahmer et al., Safety and activity of anti-PD-L1 antibody in patients with advanced cancer, The New England Journal of Medicine, 366(26):2455-2465 (2012).
Bredel et al., High-resolution genome-wide mapping of genetic alterations in human glial brain tumors, Cancer Res., 65:4088-96 (2005).
Broos et al., Particle-mediated intravenous delivery of antigen mRNA results in strong antigen-specific T-cell responses despite the induction of Type I interferon, Mol. Ther. Nucleic Acids, 5(6):e326 (2016).
Bulte, In vivo MRI cell tracking: clinical studies, American Journal of Roentgenology, 193(2):314-325 (2009).
Burg et al., Vaccines for established cancer: overcoming the challenges posed by immune evasion, Nat. Rev. Cancer, 16(4):219-233 (2016).
Campos et al., Aberrant self-renewal and quiescence contribute to the aggressiveness of glioblastoma, J. Pathol., 234:23-33 (2014).
Candelario et al., Neural stem/progenitor cells display a low requirement for oxidative metabolism independent of hypoxia inducible factor-1alpha expression, J. Neurochem., 125(3):420-9 (2013).
Caplen et al., dsRNA-mediated gene silencing in cultured Drosophila cells: a tissue culture model for the analysis of RNA interference, Gene, 252:95-105 (2000).
Caro et al., Metabolic signatures uncover distinct targets in molecular subsets of diffuse large B cell lymphoma, Cancer Cell, 22(4):547-60 (2012).
Chaffer et al., Poised chromatin at the ZEB1 promoter enables breast cancer cell plasticity and enhances tumorigenicity, Cell, 154(1):61-74 (2013).
Chandra et al., Triggering and modulation of apoptosis by oxidative stress, Free Radic Biol. Med., 29(3-4):323-33 (2000).
Charles et al., The brain tumor microenvironment, Glia., 59(8):1169-1180 (2011).
Chen et al., A restricted cell population propagates glioblastoma growth after chemotherapy, Nature, 488:522-6 (2012).
Chheda, Z.S., et al., "Novel and shared neoantigen derived from histone 3 variant H3.3K27M mutation for glioma T cell therap," Journal of Experimental Medicine, 215(1):141-157(2018).
Chickera et al., Cellular MRI as a suitable, sensitive non-invasive modality for correlating in vivo migratory efficiencies of different dendritic cell populations with subsequent immunological outcomes, Int. Immunol., 24(1):29-41 (2012).
Cho et al., A multifunctional core-shell nanoparticle for dendritic cell-based cancer immunotherapy, Nat. Nanotechnol., 6(10):675-682 (2011).
Chongsathidkiet et al., Sequestration of T cells in bone marrow in the setting of glioblastoma and other intracranial tumors, Nature Medicine, 24(9):1459-68 (2018).
Chu et al., Abnormal alpha-synuclein reduces nigral voltage-dependent anion channel 1 in sporadic and experimental Parkinson's disease, Neurobiol. Dis., 69:1-14 (2014).
Conrad et al., Intratumoral heterogeneity and intraclonal plasticity: from warburg to oxygen and back again, Neuro Oncol., 16(8):1025-6 (2014).
Crozat et al., TLR7: A new sensor of viral infection, Proc. Natl. Acad. Sci. USA, 101(18):6835-6836 (2004).
Deleyrolle et al., Evidence for label-retaining tumour-initiating cells in human glioblastoma, Brain, 134(5):1331-1343 (2011).
Deleyrolle et al., Identification and isolation of slow-dividing cells in human glioblastoma using carboxy fluorescein succinimidyl ester (CFSE), J. Vis. Exp., (62):3918 (2012).
Dembinski et al., Characterization and functional analysis of a slow cycling stem cell-like subpopulation in pancreas adenocarcinoma, Clin. Exp. Metastasis, 26(7):611-23 (2009).
Depner et al., EphrinB2 repression through ZEB2 mediates tumour invasion and anti-angiogenic resistance, Nat. Commun., 7:12329 (2016).
Dong et al., Regulation of lipid droplets by autophagy, Trends Endocrinol. Metab., 22(6):234-40 (2011).
Dutoit et al., Exploiting the glioblastoma peptidome to discover novel tumour-associated antigens for immunotherapy, Brain, 135(Pt 4):1042-54 (2012).
Elbashir et al., Duplexes of 21-nucleotide RNAs mediate RNA interference in cultured mammalian cells, Nature, 411:494-498 (2001).
Elbashir et al., RNA interference is mediated by 21- and 22-nucleotide RNAs, Genes & Development, 15(2):188-200 (2001).
Elbashir et al., RNA interference is mediated by 21- and 22-nucleotide RNAs, Genes Dev., 15:188-200 (2001).
Fecci et al., Systemic anti-CD25 monoclonal antibody administration safely enhances immunity in murine glioma without eliminating regulatory T cells, Clin. Cancer Res., 12(14 Pt 1):4294-305 (2006).
Fecci et al., Systemic CTLA-4 blockade ameliorates glioma-induced changes to the CD4+ T cell compartment without affecting regulatory T-cell function, Clin. Cancer Res., 13(7):2158-67 (2007).
Lechner et al., Immunogenicity of murine solid tumor models as a defining feature of in vivo behavior and response to immunotherapy, J. Immunother., 36(9):477-489 (2013).
Lesterhuis et al., Dynamic versus static biomarkers in cancer immune checkpoint blockade: unravelling complexity, Nat. Rev. Drug Discov., 16(4):264-272 (2017).
Lewis et al., Distinct role of macrophages in different tumor microenvironments, Cancer Res., 66(2):605-612 (2006).
Li et al., Hypoxia inducible factor-1a (HIF-1a) is required for neural stem cell maintenance and vascular stability in the adult mouse SVZ, J. Neurosci., 34(50):16713-9 (2014).
Li et al., LIpid Desaturation Is a Metabolic Marker and Therapeutic Target of Ovarian Cancer Stem Cells, Cell stem. cell, 20(3):303-314e5 (2017).
Li et al., Lipid Metabolism Fuels Cancer's Spread, Cell Metab., 25(2):228-230 (2017).
Liang et al., Nuclear FABP7 immunoreactivity is preferentially expressed in infiltrative glioma and is associated with poor prognosis in EGFR-overexpressing glioblastoma, BMC Cancer, 6:97 (2006).
Lim et al., Biocompatible polymer-nanoparticle-based bimodal imaging contrast agents for the labeling and tracking of dendritic cells, Small, 4(10):1640-1645 (2008).
Lima et al., Gene delivery mediated by cationic liposomes: from biophysical aspects to enhancement of transfection, Mol. Membr. Biol., 16(1):103-109 (1999).
Mackay et al., Multimodal imaging of dendritic cells using a novel hybrid magneto-optical nanoprobe, Nanomedicine, 7(4):489-496 (2011).
Mah et al., Improved method of recombinant AAV2 delivery for systemic targeted gene therapy, Mol. Ther., 6(1):106-112 (2002).
Mahan et al., Advanced Nanomaterials for Biological Applications, J Nanomaterials, 2018:5837276 (2018).
Mahjub et al., Recent advances in applying nanotechnologies for cancer immunotherapy, J. Contr. Rel., 288:239-263 (2018).

(56) References Cited

OTHER PUBLICATIONS

Maier et al., Biodegradable lipids enabling rapidly eliminated lipid nanoparticles for systemic delivery of RNAi therapeutics, Molecular Therapy, 21(8):1570-1578 (2013).
Marin-Valencia et al., Analysis of tumor metabolism reveals mitochondrial glucose oxidation in genetically diverse human glioblastomas in the mouse brain in vivo, Cell Metab. 15(6):827-37 (2012).
Martuscello et al., A Supplemented High-Fat Low-Carbohydrate Diet for the Treatment of Glioblastoma, Clin. Cancer Res., 22(10):2482-95 (2016).
Mashimo et al., Acetate is a bioenergetic substrate for human glioblastoma and brain metastases, Cell, 159(7):1603-14 (2014).
McGuiness, J., et al., "IMMU-07. Immunologic Targeting of DIPG With H3K27M Encoding RNA-Nanoparticles," Neuro-Oncology, 21(Supplemtn 2):1194 (2019).
Mei et al., Differential roles of unsaturated and saturated fatty acids on autophagy and apoptosis in hepatocytes, J. Pharmacol. Exp. Ther., 339:487-98 (2011).
Meng et al., Predictive biomarkers in PD-1/PD-L1 checkpoint blockade immunotherapy, Cancer Treat. Rev., 41(10):868-876 (2015).
Miao et al., EGFRvlll-specific chimeric antigen receptor T cells migrate to and kill tumor deposits infiltrating the brain parenchyma in an invasive xenograft model of glioblastoma, PloS one, 9(4):e94281 (2014).
Mitchell et al., Monoclonal antibody blockade of IL-2 receptor a during lymphopenia selectively depletes regulatory T cells in mice and humans, Blood, 118(11):3003-12 (2011).
Mitchell et al., RNA-transfected dendritic cells in cancer immunotherapy, The Journal of Clinical Investigation, 106(9):1065-9 (2000).
Mitchell et al., Tetanus toxoid and CCL3 improve dendritic cell vaccines in mice and glioblastoma patients, Nature, 519:366-369 (2015).
Moore et al., Slow-cycling therapy-resistant cancer cells, Stem. Cells Dev., 21(10):1822-30 (2012).
Morantz et al., Macrophages in experimental and human brain tumors. Part 2: studies of the macrophage content of human brain tumors, J. Neurosurg, 50(3):305-311 (1979).
Morihiro et al., Fatty acid binding protein 7 as a marker of glioma stem cells, Pathol Int., 63(11):546-53 (2013).
Mosser et al., Exploring the full spectrum of macrophage activation, Nat. Rev. Immunol., 8(12):958-969 (2008).
Mou et al., In vivo migration of dendritic cells labeled with synthetic superparamagnetic iron oxide, Int. J. Nanomedicine, 6:2633-2640 (2011).
Nair et al., Recognition and Killing of Autologous, Primary Glioblastoma Tumor Cells by Human Cytomegalovirus pp65-Specific Cytotoxic T Cells, Clin. Cancer Res., 20(10):2684-2694 (2014).
Nishino et al., Monitoring immune-checkpoint blockade: response evaluation and biomarker development, Nat. Rev. Clin. Oncol., 14(11):655-668 (2017).
Nitta et al., Proc. 14th International Congr. Chemotherapy, Kyoto, Tokyo Press, Anticancer Section 1, p. 28-30 (1985).
Noh et al., Simultaneous in vivo tracking of dendritic cells and priming of an antigen-specific immune response, Biomaterials, 32(26):6254-6263 (2011).
Noto et al., Stearoyl-CoA-desaturase 1 regulates lung cancer stemness via stabilization and nuclear localization of YAP/TAZ, Oncogene, 36(32):4671-4672 (2017).
Nykanen et al., ATP requirements and small interfering RNA structure in the RNA interference pathway, Cell, 107(3):309-321 (2001).
Oberli et al., Lipid nanoparticle assisted mrna delivery for potent cancer immunotherapy, Nano Lett., 17(3):1326-1335 (2017).
Oliva et al., Acquisition of chemoresistance in gliomas is associated with increased mitochondrial coupling and decreased ROS production, PLoS One, 6(9):e24665 (2011).
Oshimori et al., TGF-β promotes heterogeneity and drug resistance in squamous cell carcinoma, Cell, 160(5):963-976 (2015).
Osswald et al., Brain tumour cells interconnect to a functional and resistant network, Nature, 528:93-8 (2015).
Paepe, Mitochondrial markers for cancer: relevance to diagnosis, therapy, and prognosis and general understanding of malignant disease mechanisms, ISRN Pathology, 2012:Article ID 217162 (2012).
Paller et al., Sipuleucel-T for the treatment of metastatic prostate cancer: promise and challenges, Hum. Vaccin. Immunother., 8(4):509-19 (2012).
Pardall, The blockade of immune checkpoints in cancer immunotherapy, Nature Rev. Cancer, 12(4):252-264 (2012).
Pardoll, The blockade of immune checkpoints in cancer immunotherapy, Nature Rev. Cancer, 12(4):252-264 (2012).
Patel et al., Single-cell RNA-seq highlights intratumoral heterogeneity in primary glioblastoma, Science, 344:1396-401 (2014).
Pece et al., Biological and molecular heterogeneity of breast cancers correlates with their cancer stem cell content, Cell, 140(1):62-73 (2010).
Perera et al., Transcriptional control of autophagy-lysosome function drives pancreatic cancer metabolism, Nature, 524:361-5 (2015).
Phua et al., Messenger RNA (mRNA) nanoparticle tumour vaccination, Nanoscale, 6(14):7715-7729 (2014).
Poon et al., Glioblastoma-associated microglia and macrophages: targets for therapies to improve prognosis, Brain, 140(6):1548-1560 (2017).
Pyzer et al., Clinical trials of dendritic cell-based cancer vaccines in hematologic malignancies, Hum. Vaccin. Immunother., 10(11):3125-3131 (2014).
Qi et al., ZEB2 mediates multiple pathways regulating cell proliferation, migration, invasion, and apoptosis in glioma, PLoS One, 7(6):e38842 (2012).
Fiedler et al., mRNA Cancer Vaccines, Rece. Resu. Canc. Res., 209:61-85 (2016).
Filley et al., Recurrent glioma clinical trial, CheckMate-143: the game is not over yet, Oncotarget., 8(53):91779-91794 (2017).
Fire et al., Potent and specific genetic interference by double-stranded RNA in caenorhabditis elegans, Nature, 391:806-811 (1998).
Flores et al., Novel role of hematopoietic stem cells in immunologic rejection of malignant gliomas, Oncoinununology, 4(3):e994374 (2015).
Furuhashi et al., Treatment of diabetes and atherosclerosis by inhibiting fatty-acid-binding protein aP2, Nature, 447(7147):959-65 (2007).
Gaillard et al., The role of immune checkpoint inhibition in the treatment of ovarian cancer, Gynecol. Oncol. Res. Pract., 3:11 (2016).
Gao et al., CD24+ cells from hierarchically organized ovarian cancer are enriched in cancer stem cells, Oncogene, 29:2672-2680 (2010).
Garon et al., Pembrolizumab for the treatment of non-small-cell lung cancer, N. Engl. J. Med., 372(21):2018-2028 (2015).
Gilboa et al., Cancer immunotherapy with mRNA-transfected dendritic cells, J. Immunol. Rev., 199:251-263 (2004).
Graham et al., Primitive, quiescent, Philadelphia-positive stem cells from patients with chronic myeloid leukemia are insensitive to STI571 in vitro, Blood, 99(1):319-25 (2002).
Grippin et al., Translational nanoparticle engineering for cancer vaccines, Oncoimmunology, 6(10):e1290036 (2017).
Grobner et al., The landscape of genomic alterations across childhood cancers, Nature, 555:321-327 (2018).
Gros et al., PD-1 identifies the patient-specific CD8? tumor-reactive repertoire infiltrating human tumors, The Journal of Clinical Investigation, 124(5):2246-2259 (2014).
Grupp et al., Chimeric antigen receptor-modified T cells for acute lymphoid leukemia, The New England Journal of Medicine, 368(16):1509-18 (2013).
Hammond et al., An RNA-directed nuclease mediates post-transcriptional gene silencing in drosophila cells, Nature, 404:293-296 (2000).
Hellmann et al., Nivolumab plus ipilimumab as first-line treatment for advanced non-small-cell lung cancer (CheckMate 012): results of an open-label, phase 1, multicohort study, Lancet Oncol., 18(1):31-41 (2017).

(56) References Cited

OTHER PUBLICATIONS

Hensley et al., Metabolic Heterogeneity in Human Lung Tumors, Cell, 164(4):681-94 (2016).
Heyes et al., Cationic lipid saturation influences intracellular delivery of encapsulated nucleic acids, J. Controlled Release, 107(2):276-287 (2005).
Hilf et al., Actively personalized vaccination trial for newly diagnosed glioblastoma, Nature, 565:240-245 (2019).
Hinrichs, Exploiting the curative potential of adoptive T-cell therapy for cancer, Immunological reviews, 257(1):56-71 (2014).
Hoang-Minh et al., Disruption of KIF3A in patient-derived glioblastoma cells: effects on ciliogenesis, hedgehog sensitivity, and tumorigenesis, Oncotarget., 7(6):7029-43 (2016).
Hoang-Minh et al., Infiltrative and drug-resistant slow-cycling cells support metabolic heterogeneity in glioblastoma, EMBO J., 37(23):e98772 (2018).
Hoogenboom et al., The supramolecular assemblies of voltage-dependent anion channels in the native membrane! J. Mol. Biol., 370(2):246-55 (2007).
Hutvagner et al., RNAi: nature abhors a double-strand, Curr. Opin. Genet. Dev., 12(2):225-232 (2002).
International Application No. PCT/US19/050850, International Search Report and Written Opinion, mailed Feb. 3, 2020.
International Application No. PCT/US19/31385, International Preliminary Report on Patentability, mailed Nov. 19, 2020.
International Application No. PCT/US19/31385, International Search Report and Written Opinion, mailed Sep. 20, 2019.
International Application No. PCT/US19/50850, International Preliminary Report on Patentability, mailed Mar. 25, 2021.
International Application No. PCT/US19/46618, International Preliminary Report on Patentability, mailed Feb. 25, 2021.
International Application No. PCT/US19/46618, International Search Report and Written Opinion, mailed Nov. 29, 2019.
International Application No. PCT/US20/31096, International Preliminary Report on Patentability, mailed Nov. 11, 2021.
International Application No. PCT/US20/31096, International Search Report and Written Opinion, mailed Nov. 17, 2020.
International Application No. PCT/US20/42606, International Preliminary Report on Patentability, mailed Feb. 3, 2022.
International Application No. PCT/US20/42606, International Search Report and Written Opinion, mailed Dec. 2, 2020.
Jayararna et al., Maximizing the potency of siRNA lipid nanoparticles for hepatic gene silencing in vivo, Angew. Chem. Int. Ed., 51(34):8529-8533 (2012).
Jegga et al., Systems biology of the autophagy-lysosomal pathway, Autophagy, 7(5):477-89 (2011).
Jensen et al., Tumor vol. in subcutaneous mouse xenografts measured by microCT is more accurate and reproducible than determined by 18F-FDG-microPET or external caliper, BMC medical imaging, 8:16 (2008).
Jin et al., Magnetic Enrichment of Dendritic Cell Vaccine in Lymph Node with Fluorescent-Magnetic Nanoparticles Enhanced Cancer Immunotherapy, Theranostics, 6(11):2000-2014 (2016).
Kaczocha et al., Inhibition of fatty acid binding proteins elevates brain anandamide levels and produces analgesia, PLoS One, 9(4):e94200 (2014).
Kauffman et al., Optimization of Lipid Nanoparticle Formulations for mRNA Delivery in Vivo with Fractional Factorial and Definitive Screening Designs, Nano Lett., 15(11):7300-7306 (2015).
Kim et al., Molecular and immunological analysis of genetic prostate specific antigen (PSA) vaccine, Oncogene, 17(24):3125-35 (1998).
Kleponis et al., Fueling the engine and releasing the break: combinational therapy of cancer vaccines and immune checkpoint inhibitors, Cancer Biol. Med., 12(3):201-218 (2015).
Koppenol et al., Otto Warburg's contributions to current concepts of cancer metabolism, Nature, 11(5):325-37 (2011).
Kranz et al., Systemic RNA delivery to dendritic cells exploits antiviral defence for cancer immunotherapy, Nat., 534(7607):396-401 (2016).
Lagadinou et al., BCL-2 inhibition targets oxidative phosphorylation and selectively eradicates quiescent human leukemia stem cells, Cell Stem. Cell, 12(3):329-41 (2013).
Lan et al., Fate mapping of human glioblastoma reveals an invariant stem cell hierarchy, Nature, 549(7671):227-232 (2017).
Landen et al., Intraperitoneal delivery of liposomal siRNA for therapy of advanced ovarian cancer, Cancer Biology & Therapy, 5(12):1708-1713 (2006).
Landriscina et al., Adaptation to oxidative stress, chemoresistance, and cell survival, Antioxid Redox Signal, 11(11):2701-16 (2009).
Larkin et al., Combined Nivolumab and Ipilimumab or Monotherapy in Untreated Melanoma, N. Engl. J. Med., 373(1):23-34 (2015).
Learn et al., Profiling of CD4+, CD8+, and CD4+CD25+CD45RO+ FoxP3+ T cells in patients with malignant glioma reveals differential expression of the immunologic transcriptome compared with T cells from healthy volunteers, Clin. Cancer Res., 12(24):7306-15 (2206).
Kar et al., "Current Methods for the Prediction of T-Cell Epitopes," Peptide Science, 110(2):e24046 (2018).

* cited by examiner

Figure 1

Input = Query Sequence = GKAP*RKQLATKAARMSAPSTGGVKK*PHRY

Query Sequence = SEQ ID NO: 23
Underlined, Italicized Sequence = SEQ ID NO: 15

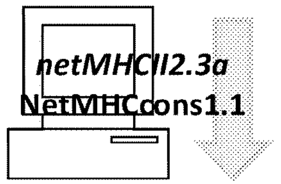

1. Generation of possible 15-mer peptide sequences of Query Sequence.
2. Predicts MHC Class II-restricted epitopes of the 15-mer peptide sequences.
3. Ranks the strength of the binding of the epitope to MHC Class II molecules.

| Allele | pos | peptide | core | Of | 1-log50k(aff) | affinity(nM) | %Rank | Relia | Identity | Bind Level | Peptide SEQ ID NO: | Core SEQ ID NO: |
|---|---|---|---|---|---|---|---|---|---|---|---|---|
| H-2-IAb | 1 | GKAPRKQLATKAARM | RKQLATKAA | 4 | 0.2883 | 3210.0 | 12.00 | 0.51 | Seq 1 | | 24 | 39 |
| H-2-IAb | 2 | KAPRKQLATKAARMS | RKQLATKAA | 3 | 0.3169 | 1622.0 | 9.00 | 0.41 | Seq 1 | | 25 | 39 |
| H-2-IAb | 3 | APRKQLATKAARMSA | RKQLATKAA | 2 | 0.3336 | 1353.7 | 7.50 | 0.32 | Seq 1 | | 26 | 39 |
| H-2-IAb | 4 | PRKQLATKAARMSAP | LATKAARMS | 4 | 0.3783 | 834.7 | 5.00 | 0.35 | Seq 1 | | 27 | 40 |
| H-2-IAb | 5 | RKQLATKAARMSAPS | LATKAARMS | 3 | 0.3882 | 749.5 | 4.50 | 0.38 | Seq 1 | WB | 28 | 40 |
| H-2-IAb | 6 | KQLATKAARMSAPST | LATKAARMS | 2 | 0.4202 | 530.5 | 3.50 | 0.34 | Seq 1 | WB | 29 | 40 |
| H-2-IAb | 7 | QLATKAARMSAPSTG | ARMSAPSTG | 6 | 0.5200 | 180.0 | 1.00 | 0.41 | Seq 1 | SB | 30 | 41 |
| H-2-IAb | 8 | LATKAARMSAPSTGG | ARMSAPSTG | 5 | 0.5143 | 191.6 | 1.00 | 0.44 | Seq 1 | SB | 31 | 41 |
| H-2-IAb | 9 | ATKAARMSAPSTGGV | ARMSAPSTG | 4 | 0.5013 | 220.5 | 1.20 | 0.49 | Seq 1 | SB | 32 | 41 |
| H-2-IAb | 10 | TKAARMSAPSTGGVK | ARMSAPSTG | 3 | 0.4992 | 225.6 | 1.30 | 0.45 | Seq 1 | SB | 33 | 41 |
| H-2-IAb | 11 | KAARMSAPSTGGVKK | ARMSAPSTG | 2 | 0.4783 | 282.7 | 1.60 | 0.50 | Seq 1 | SB | 34 | 41 |
| H-2-IAb | 12 | AARMSAPSTGGVKKP | ARMSAPSTG | 1 | 0.4456 | 403.0 | 2.50 | 0.47 | Seq 1 | WB | 35 | 41 |
| H-2-IAb | 13 | ARMSAPSTGGVKKPH | ARMSAPSTG | 0 | 0.3498 | 1135.2 | 6.50 | 0.34 | Seq 1 | | 36 | 41 |
| H-2-IAb | 14 | RMSAPSTGGVKKPHR | SAPSTGGVK | 3 | 0.2299 | 4156.5 | 20.00 | 0.47 | Seq 1 | | 37 | 42 |
| H-2-IAb | 15 | MSAPSTGGVKKPHRY | SAPSTGGVK | 1 | 0.2056 | 5403.0 | 24.00 | 0.51 | Seq 1 | | 38 | 42 |

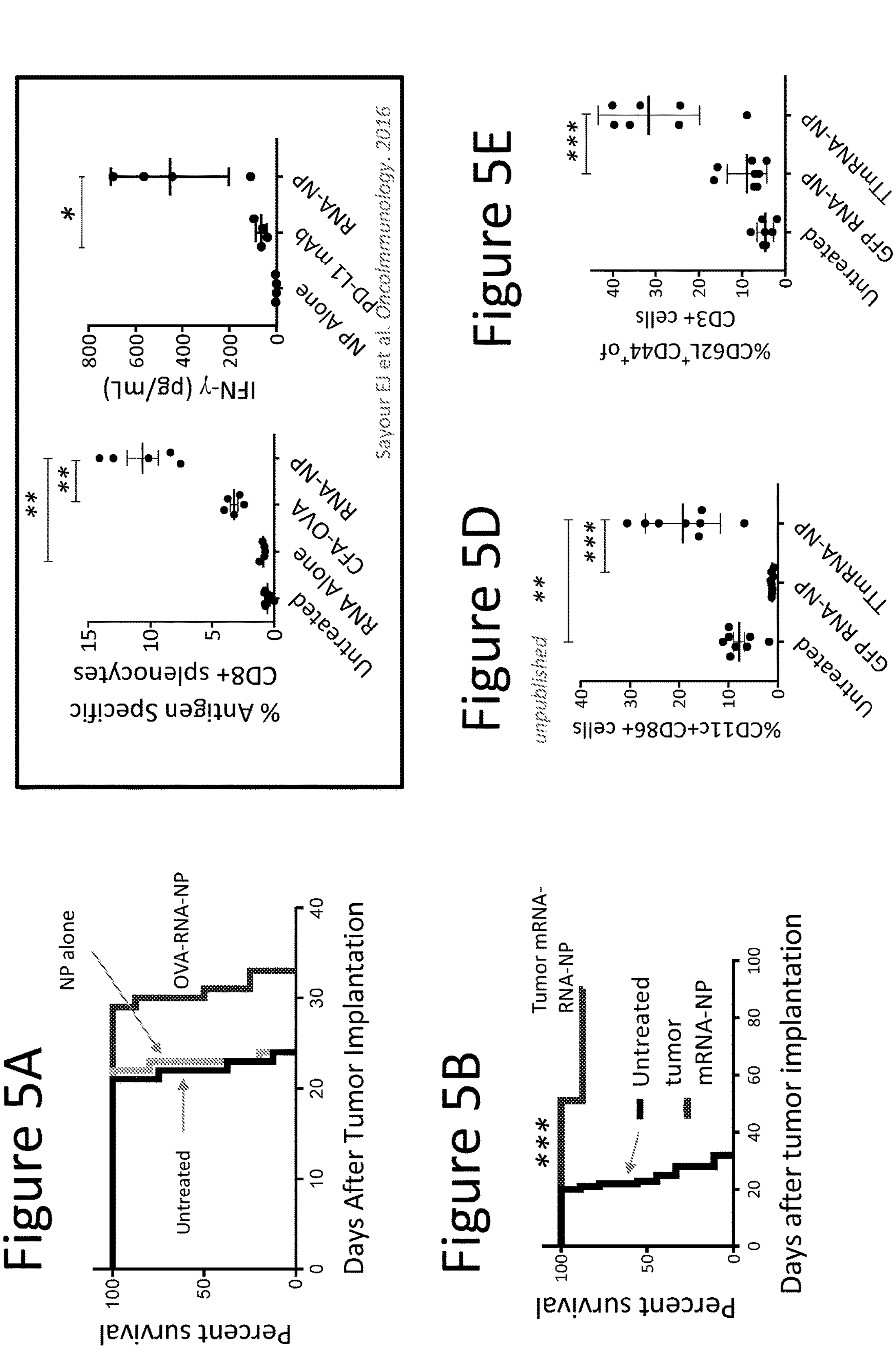
Figure 5A
Percent survival
Days After Tumor Implantation
Untreated
NP alone
OVA-RNA-NP
Figure 5B
Percent survival
Days after tumor implantation
***
Untreated
tumor mRNA-NP
Tumor mRNA-RNA-NP
Figure 5C
% Antigen Specific CD8+ splenocytes
Untreated
RNA Alone
CFA-OVA
OVA RNA-NP
IFN-γ (pg/mL)
NP Alone
PD-L1 mAb
RNA-NP
Sayour EJ et al. Oncoimmunology. 2016
Figure 5D
%CD11c+CD86+ cells
Untreated
GFP RNA-NP
TTmRNA-NP
unpublished
Figure 5E
%CD62L+CD44+ of CD3+ cells
Untreated
GFP RNA-NP
TTmRNA-NP

SEQUENCE LISTING

```
<160> NUMBER OF SEQ ID NOS: 42

<210> SEQ ID NO 1
<211> LENGTH: 135
<212> TYPE: PRT
<213> ORGANISM: Artificial Sequence
<220> FEATURE:
<223> OTHER INFORMATION: Synthetic Polypeptide

<400> SEQUENCE: 1

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Met Ser Ala Pro Ser Thr
            20                  25                  30

Gly Gly Val Lys Lys Pro His Arg Tyr Arg Pro Gly Thr Val Ala Leu
        35                  40                  45

Arg Glu Ile Arg Arg Tyr Gln Lys Ser Thr Glu Leu Leu Ile Arg Lys
    50                  55                  60

Leu Pro Phe Gln Arg Leu Val Arg Glu Ile Ala Gln Asp Phe Lys Thr
65                  70                  75                  80

Asp Leu Arg Phe Gln Ser Ala Ala Ile Gly Ala Leu Gln Glu Ala Ser
                85                  90                  95

Glu Ala Tyr Leu Val Gly Leu Phe Glu Asp Thr Asn Leu Cys Ala Ile
            100                 105                 110

His Ala Lys Arg Val Thr Ile Met Pro Lys Asp Ile Gln Leu Ala Arg
        115                 120                 125

Arg Ile Arg Gly Glu Arg Ala
    130                 135


<210> SEQ ID NO 2
<211> LENGTH: 3000
<212> TYPE: DNA
<213> ORGANISM: Artificial Sequence
<220> FEATURE:
<223> OTHER INFORMATION: Synthetic Polynucleotide

<400> SEQUENCE: 2

ctaatacgac tcactatagg gagacaagct tatggctcgt acaaagcaga ctgcccgcaa      60

atcgaccggt ggtaaagcac ccaggaagca actggctaca aaagccgctc gcaagagtgc     120

gccctctact ggaggggtga agaaacctca tcgttacagg cctggtactg tggcgctccg     180

tgaaattaga cgttatcaga agtccactga acttctgatt cgcaaacttc ccttccagcg     240

tctggtgcga gaaattgctc aggactttaa aacagatctg cgcttccaga gcgcagctat     300

cggtgctttg caggaggcaa gtgaggccta tctggttggc ctttttgaag acaccaacct     360

gtgtgctatc catgccaaac gtgtaacaat tatgccaaaa gacatccagc tagcacgccg     420

catacgtgga gaacgtgctt aagaattctt aattaaaaaa aaaaaaaaaa aaaaaaaaaa     480

aaaaaaaaaa aaaaaaaaaa aaaaaaaaaa aaaaaactag tggcgcctga tgcggtattt     540
```

-continued

```
tctccttacg catctgtgcg gtatttcaca ccgcatatgg tgcactctca gtacaatctg    600
ctctgatgcc gcatagttaa gccagccccg acacccgcca acacccgctg acgcgccctg    660
acgggcttgt ctgctcccgg catccgctta cagacaagct gtgaccgtct ccgggagctg    720
catgtgtcag aggttttcac cgtcatcacc gaaacgcgcg agacgaaagg gcctcgtgat    780
acgcctattt ttataggtta atgtcatgat aataatggtt tcttagacgt caggtggcac    840
ttttcgggga aatgtgcgcg gaacccctat ttgtttattt ttctaaatac attcaaatat    900
gtatccgctc atgagacaat aaccctgata aatgcttcaa taatattgaa aaaggaagag    960
tatgagtatt caacatttcc gtgtcgccct tattcccttt tttgcggcat tttgccttcc   1020
tgtttttgct cacccagaaa cgctggtgaa agtaaaagat gctgaagatc agttgggtgc   1080
acgagtgggt tacatcgaac tggatctcaa cagcggtaag atccttgaga gttttcgccc   1140
cgaagaacgt tttccaatga tgagcacttt taaagttctg ctatgtggcg cggtattatc   1200
ccgtattgac gccgggcaag agcaactcgg tcgccgcata cactattctc agaatgactt   1260
ggttgagtac tcaccagtca cagaaaagca tcttacggat ggcatgacag taagagaatt   1320
atgcagtgct gccataacca tgagtgataa cactgcggcc aacttacttc tgacaacgat   1380
cggaggaccg aaggagctaa ccgctttttt gcacaacatg ggggatcatg taactcgcct   1440
tgatcgttgg gaaccggagc tgaatgaagc cataccaaac gacgagcgtg acaccacgat   1500
gcctgtagca atgccaacaa cgttgcgcaa actattaact ggcgaactac ttactctagc   1560
ttcccggcaa caattaatag actggatgga ggcggataaa gttgcaggac cacttctgcg   1620
ctcggccctt ccggctggct ggtttattgc tgataaatct ggagccggtg agcgtgggtc   1680
tcgcggtatc attgcagcac tggggccaga tggtaagccc tcccgtatcg tagttatcta   1740
cacgacgggg agtcaggcaa ctatggatga acgaaataga cagatcgctg agataggtgc   1800
ctcactgatt aagcattggt aactgtcaga ccaagtttac tcatatatac tttagattga   1860
tttaaaactt catttttaat ttaaaaggat ctaggtgaag atcctttttg ataatctcat   1920
gaccaaaatc ccttaacgtg agttttcgtt ccactgagcg tcagaccccg tagaaaagat   1980
caaaggatct tcttgagatc cttttttttct gcgcgtaatc tgctgcttgc aaacaaaaaa   2040
accaccgcta ccagcggtgg tttgtttgcc ggatcaagag ctaccaactc tttttccgaa   2100
ggtaactggc ttcagcagag cgcagatacc aaatactgtc cttctagtgt agccgtagtt   2160
aggccaccac ttcaagaact ctgtagcacc gcctacatac ctcgctctgc taatcctgtt   2220
accagtggct gctgccagtg gcgataagtc gtgtcttacc gggttggact caagacgata   2280
gttaccggat aaggcgcagc ggtcgggctg aacggggggt tcgtgcacac agcccagctt   2340
ggagcgaacg acctacaccg aactgagata cctacagcgt gagctatgag aaagcgccac   2400
gcttcccgaa gggagaaagg cggacaggta tccggtaagc ggcagggtcg gaacaggaga   2460
gcgcacgagg gagcttccag ggggaaacgc ctggtatctt tatagtcctg tcgggtttcg   2520
ccacctctga cttgagcgtc gatttttgtg atgctcgtca ggggggcgga gcctatcgaa   2580
aaacgccagc aacgcggcct ttttacggtt cctggccttt tgctggcctt ttgctcacat   2640
gttctttcct gcgttatccc ctgattctgt ggataaccgt attaccgcct ttgagtgagc   2700
tgataccgct cgccgcagcc gaacgaccga gcgcagcgag tcagtgagcg aggaagcgga   2760
agagcgccca atacgcaaac cgcctctccc cgcgcgttgg ccgattcatt aatgcagctg   2820
gcacgacagg tttcccgact cgaaagcggg cagtgagcgc aacgcaatta atgtgagtta   2880
```

-continued

```
gctcactcat taggcacccc aggctttaca ctttatgctt ccggctcgta tgttgtgtgg   2940

aattgtgagc ggataacaat ttcacacagg aaacagctat gaccatgatt acgccaagct   3000


<210> SEQ ID NO 3
<211> LENGTH: 502
<212> TYPE: DNA
<213> ORGANISM: Artificial Sequence
<220> FEATURE:
<223> OTHER INFORMATION: Synthetic Polynucleotide

<400> SEQUENCE: 3

gggagacaag cuuauggcuc guacaaagca gacugcccgc aaaucgaccg gugguaaagc     60

acccaggaag caacuggcua caaaagccgc ucgcaagagu gcgcccucua cuggaggggu    120

gaagaaaccu caucguuaca ggccugguac uguggcgcuc cgugaaauua gacguuauca    180

gaaguccacu gaacuucuga uucgcaaacu ucccuuccag cgucuggugc gagaaauugc    240

ucaggacuuu aaaacagauc ugcgcuucca gagcgcagcu aucggugcuu ugcaggaggc    300

aagugaggcc uaucugguug gccuuuuuga agacaccaac cugugugcua uccaugccaa    360

acguguaaca auuaugccaa aagacaucca gcuagcacgc cgcauacgug gagaacgugc    420

uuaagaauuc uuaauuaaaa aaaaaaaaaa aaaaaaaaaa aaaaaaaaaa aaaaaaaaaa    480

aaaaaaaaaa aaaaaaaacu ag                                             502


<210> SEQ ID NO 4
<211> LENGTH: 136
<212> TYPE: PRT
<213> ORGANISM: Artificial Sequence
<220> FEATURE:
<223> OTHER INFORMATION: Synthetic Polypeptide

<400> SEQUENCE: 4

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ser
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ala Ala Ile Gly Ala Leu Gln Glu Ala
                85                  90                  95

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135


<210> SEQ ID NO 5
<211> LENGTH: 3000
<212> TYPE: DNA
<213> ORGANISM: Artificial Sequence
<220> FEATURE:
<223> OTHER INFORMATION: Synthetic Polynucleotide

<400> SEQUENCE: 5
```

-continued

```
ctaatacgac tcactatagg gagacaagct tatggctcgt acaaagcaga ctgcccgcaa     60
atcgaccggt ggtaaagcac ccaggaagca actggctaca aaagccgctc gcatgagtgc    120
gccctctact ggaggggtga agaaacctca tcgttacagg cctggtactg tggcgctccg    180
tgaaattaga cgttatcaga agtccactga acttctgatt cgcaaacttc ccttccagcg    240
tctggtgcga gaaattgctc aggactttaa aacagatctg cgcttccaga gcgcagctat    300
cggtgctttg caggaggcaa gtgaggccta tctggttggc ctttttgaag acaccaacct    360
gtgtgctatc catgccaaac gtgtaacaat tatgccaaaa gacatccagc tagcacgccg    420
catacgtgga gaacgtgctt aagaattctt aattaaaaaa aaaaaaaaaa aaaaaaaaaa    480
aaaaaaaaaa aaaaaaaaaa aaaaaaaaaa aaaaaaactag tggcgcctga tgcggtattt    540
tctccttacg catctgtgcg gtatttcaca ccgcatatgg tgcactctca gtacaatctg    600
ctctgatgcc gcatagttaa gccagccccg acacccgcca acacccgctg acgcgccctg    660
acgggcttgt ctgctcccgg catccgctta cagacaagct gtgaccgtct ccgggagctg    720
catgtgtcag aggttttcac cgtcatcacc gaaacgcgcg agacgaaagg gcctcgtgat    780
acgcctattt ttataggtta atgtcatgat aataatggtt tcttagacgt caggtggcac    840
ttttcgggga aatgtgcgcg gaacccctat ttgtttattt ttctaaatac attcaaatat    900
gtatccgctc atgagacaat aaccctgata aatgcttcaa taatattgaa aaaggaagag    960
tatgagtatt caacatttcc gtgtcgccct tattcccttt tttgcggcat tttgccttcc   1020
tgtttttgct cacccagaaa cgctggtgaa agtaaaagat gctgaagatc agttgggtgc   1080
acgagtgggt tacatcgaac tggatctcaa cagcggtaag atccttgaga gttttcgccc   1140
cgaagaacgt tttccaatga tgagcacttt taaagttctg ctatgtggcg cggtattatc   1200
ccgtattgac gccgggcaag agcaactcgg tcgccgcata cactattctc agaatgactt   1260
ggttgagtac tcaccagtca cagaaaagca tcttacggat ggcatgacag taagagaatt   1320
atgcagtgct gccataacca tgagtgataa cactgcggcc aacttacttc tgacaacgat   1380
cggaggaccg aaggagctaa ccgctttttt gcacaacatg ggggatcatg taactcgcct   1440
tgatcgttgg gaaccggagc tgaatgaagc cataccaaac gacgagcgtg acaccacgat   1500
gcctgtagca atgccaacaa cgttgcgcaa actattaact ggcgaactac ttactctagc   1560
ttcccggcaa caattaatag actggatgga ggcggataaa gttgcaggac cacttctgcg   1620
ctcggccctt ccggctggct ggtttattgc tgataaatct ggagccggtg agcgtgggtc   1680
tcgcggtatc attgcagcac tggggccaga tggtaagccc tcccgtatcg tagttatcta   1740
cacgacgggg agtcaggcaa ctatggatga acgaaataga cagatcgctg agataggtgc   1800
ctcactgatt aagcattggt aactgtcaga ccaagtttac tcatatatac tttagattga   1860
tttaaaactt catttttaat ttaaaaggat ctaggtgaag atcctttttg ataatctcat   1920
gaccaaaatc ccttaacgtg agttttcgtt ccactgagcg tcagaccccg tagaaaagat   1980
caaaggatct tcttgagatc ctttttttct gcgcgtaatc tgctgcttgc aaacaaaaaa   2040
accaccgcta ccagcggtgg tttgtttgcc ggatcaagag ctaccaactc tttttccgaa   2100
ggtaactggc ttcagcagag cgcagatacc aaatactgtc cttctagtgt agccgtagtt   2160
aggccaccac ttcaagaact ctgtagcacc gcctacatac ctcgctctgc taatcctgtt   2220
accagtggct gctgccagtg gcgataagtc gtgtcttacc gggttggact caagacgata   2280
gttaccggat aaggcgcagc ggtcgggctg aacggggggt tcgtgcacac agcccagctt   2340
ggagcgaacg acctacaccg aactgagata cctacagcgt gagctatgag aaagcgccac   2400
```

-continued

```
gcttcccgaa gggagaaagg cggacaggta tccggtaagc ggcagggtcg gaacaggaga   2460

gcgcacgagg gagcttccag ggggaaacgc ctggtatctt tatagtcctg tcgggtttcg   2520

ccacctctga cttgagcgtc gatttttgtg atgctcgtca ggggggcgga gcctatcgaa   2580

aaacgccagc aacgcggcct ttttacggtt cctggccttt tgctggcctt ttgctcacat   2640

gttctttcct gcgttatccc ctgattctgt ggataaccgt attaccgcct ttgagtgagc   2700

tgataccgct cgccgcagcc gaacgaccga gcgcagcgag tcagtgagcg aggaagcgga   2760

agagcgccca atacgcaaac cgcctctccc cgcgcgttgg ccgattcatt aatgcagctg   2820

gcacgacagg tttcccgact cgaaagcggg cagtgagcgc aacgcaatta atgtgagtta   2880

gctcactcat taggcacccc aggctttaca ctttatgctt ccggctcgta tgttgtgtgg   2940

aattgtgagc ggataacaat ttcacacagg aaacagctat gaccatgatt acgccaagct   3000
```

<210> SEQ ID NO 6
<211> LENGTH: 502
<212> TYPE: DNA
<213> ORGANISM: Artificial Sequence
<220> FEATURE:
<223> OTHER INFORMATION: Synthetic Polynucleotide

<400> SEQUENCE: 6

```
gggagacaag cuuauggcuc guacaaagca gacugcccgc aaaucgaccg gugguaaagc     60

acccaggaag caacuggcua caaaagccgc ucgcaugagu gcgcccucua cuggaggggu    120

gaagaaaccu caucguuaca ggccugguac uguggcgcuc cgugaaauua gacguuauca    180

gaaguccacu gaacuucuga uucgcaaacu ucccuuccag cgucuggugc gagaaauugc    240

ucaggacuuu aaaacagauc ugcgcuucca gagcgcagcu aucggugcuu ugcaggaggc    300

aagugaggcc uaucugguug gccuuuuuga agacaccaac cugugugcua uccaugccaa    360

acguguaaca auuaugccaa aagacaucca gcuagcacgc cgcauacgug gagaacgugc    420

uuaagaauuc uuaauuaaaa aaaaaaaaaa aaaaaaaaaa aaaaaaaaaa aaaaaaaaaa    480

aaaaaaaaaa aaaaaaaacu ag                                             502
```

<210> SEQ ID NO 7
<211> LENGTH: 136
<212> TYPE: PRT
<213> ORGANISM: Artificial Sequence
<220> FEATURE:
<223> OTHER INFORMATION: Synthetic Polypeptide

<400> SEQUENCE: 7

```
Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Met Ser Ala Pro Ser
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ala Ala Ile Gly Ala Leu Gln Glu Ala
                85                  90                  95

Ser Glu Ala Tyr Leu Val Gly Leu Phe Glu Asp Thr Asn Leu Cys Ala
            100                 105                 110
```

```
Ile His Ala Lys Arg Val Thr Ile Met Pro Lys Asp Ile Gln Leu Ala
        115                 120                 125

Arg Arg Ile Arg Gly Glu Arg Ala
    130                 135


<210> SEQ ID NO 8
<211> LENGTH: 2670
<212> TYPE: DNA
<213> ORGANISM: Artificial Sequence
<220> FEATURE:
<223> OTHER INFORMATION: Synthetic Polynucleotide

<400> SEQUENCE: 8

ctaatacgac tcactatagg gagacaagct tatggcaccc aggaagcaac tggctacaaa     60

agccgctcgc aagagtgcgc cctctactgg aggggtgaag aaacctcatt aagaattctt    120

aattaaaaaa aaaaaaaaaa aaaaaaaaaa aaaaaaaaaa aaaaaaaaaa aaaaaaaaaa    180

aaaaaactag tggcgcctga tgcggtattt tctccttacg catctgtgcg gtatttcaca    240

ccgcatatgg tgcactctca gtacaatctg ctctgatgcc gcatagttaa gccagccccg    300

acacccgcca acacccgctg acgcgccctg acgggcttgt ctgctcccgg catccgctta    360

cagacaagct gtgaccgtct ccgggagctg catgtgtcag aggttttcac cgtcatcacc    420

gaaacgcgcg agacgaaagg gcctcgtgat acgcctattt ttataggtta atgtcatgat    480

aataatggtt tcttagacgt caggtggcac ttttcgggga aatgtgcgcg gaacccctat    540

ttgtttattt ttctaaatac attcaaatat gtatccgctc atgagacaat aaccctgata    600

aatgcttcaa taatattgaa aaaggaagag tatgagtatt caacatttcc gtgtcgccct    660

tattcccttt tttgcggcat tttgccttcc tgtttttgct cacccagaaa cgctggtgaa    720

agtaaaagat gctgaagatc agttgggtgc acgagtgggt tacatcgaac tggatctcaa    780

cagcggtaag atccttgaga gttttcgccc cgaagaacgt tttccaatga tgagcacttt    840

taaagttctg ctatgtggcg cggtattatc ccgtattgac gccgggcaag agcaactcgg    900

tcgccgcata cactattctc agaatgactt ggttgagtac tcaccagtca cagaaaagca    960

tcttacggat ggcatgacag taagagaatt atgcagtgct gccataacca tgagtgataa   1020

cactgcggcc aacttacttc tgacaacgat cggaggaccg aaggagctaa ccgctttttt   1080

gcacaacatg ggggatcatg taactcgcct tgatcgttgg gaaccggagc tgaatgaagc   1140

cataccaaac gacgagcgtg acaccacgat gcctgtagca atgccaacaa cgttgcgcaa   1200

actattaact ggcgaactac ttactctagc ttcccggcaa caattaatag actggatgga   1260

ggcggataaa gttgcaggac cacttctgcg ctcggccctt ccggctggct ggtttattgc   1320

tgataaatct ggagccggtg agcgtgggtc tcgcggtatc attgcagcac tggggccaga   1380

tggtaagccc tcccgtatcg tagttatcta cacgacgggg agtcaggcaa ctatggatga   1440

acgaaataga cagatcgctg agataggtgc ctcactgatt aagcattggt aactgtcaga   1500

ccaagtttac tcatatatac tttagattga tttaaaactt catttttaat ttaaaaggat   1560

ctaggtgaag atcctttttg ataatctcat gaccaaaatc ccttaacgtg agttttcgtt   1620

ccactgagcg tcagaccccg tagaaaagat caaaggatct tcttgagatc cttttttct   1680

gcgcgtaatc tgctgcttgc aaacaaaaaa accaccgcta ccagcggtgg tttgtttgcc   1740

ggatcaagag ctaccaactc tttttccgaa ggtaactggc ttcagcagag cgcagatacc   1800

aaatactgtc cttctagtgt agccgtagtt aggccaccac ttcaagaact ctgtagcacc   1860
```

-continued

```
gcctacatac ctcgctctgc taatcctgtt accagtggct gctgccagtg gcgataagtc   1920

gtgtcttacc gggttggact caagacgata gttaccggat aaggcgcagc ggtcgggctg   1980

aacggggggt tcgtgcacac agcccagctt ggagcgaacg acctacaccg aactgagata   2040

cctacagcgt gagctatgag aaagcgccac gcttcccgaa gggagaaagg cggacaggta   2100

tccggtaagc ggcagggtcg gaacaggaga gcgcacgagg gagcttccag ggggaaacgc   2160

ctggtatctt tatagtcctg tcgggtttcg ccacctctga cttgagcgtc gatttttgtg   2220

atgctcgtca ggggggcgga gcctatcgaa aaacgccagc aacgcggcct ttttacggtt   2280

cctggccttt tgctggcctt ttgctcacat gttctttcct gcgttatccc ctgattctgt   2340

ggataaccgt attaccgcct ttgagtgagc tgataccgct cgccgcagcc gaacgaccga   2400

gcgcagcgag tcagtgagcg aggaagcgga agagcgccca atacgcaaac cgcctctccc   2460

cgcgcgttgg ccgattcatt aatgcagctg gcacgacagg tttcccgact cgaaagcggg   2520

cagtgagcgc aacgcaatta atgtgagtta gctcactcat taggcacccc aggctttaca   2580

ctttatgctt ccggctcgta tgttgtgtgg aattgtgagc ggataacaat ttcacacagg   2640

aaacagctat gaccatgatt acgccaagct                                     2670
```

```
<210> SEQ ID NO 9
<211> LENGTH: 172
<212> TYPE: DNA
<213> ORGANISM: Artificial Sequence
<220> FEATURE:
<223> OTHER INFORMATION: Synthetic Polynucleotide

<400> SEQUENCE: 9

gggagacaag cuuauggcac ccaggaagca acuggcuaca aaagccgcuc gcaagagugc     60

gcccucuacu ggaggggguga agaaaccuca uuaagaauuc uuaauuaaaa aaaaaaaaaa    120

aaaaaaaaaa aaaaaaaaaa aaaaaaaaaa aaaaaaaaaa aaaaaaaacu ag             172
```

```
<210> SEQ ID NO 10
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 10

Met Ala Pro Arg Lys Gln Leu Ala Thr Lys Ala Ala Arg Lys Ser Ala
1               5                   10                  15

Pro Ser Thr Gly Gly Val Lys Lys Pro His
            20                  25
```

```
<210> SEQ ID NO 11
<211> LENGTH: 2670
<212> TYPE: DNA
<213> ORGANISM: Artificial Sequence
<220> FEATURE:
<223> OTHER INFORMATION: Synthetic Polynucleotide

<400> SEQUENCE: 11

ctaatacgac tcactatagg gagacaagct tatggcaccc aggaagcaac tggctacaaa     60

agccgctcgc atgagtgcgc cctctactgg aggggtgaag aaacctcatt aagaattctt    120

aattaaaaaa aaaaaaaaaa aaaaaaaaaa aaaaaaaaaa aaaaaaaaaa aaaaaaaaaa    180

aaaaaactag tggcgcctga tgcggtattt tctccttacg catctgtgcg gtatttcaca    240

ccgcatatgg tgcactctca gtacaatctg ctctgatgcc gcatagttaa gccagccccg    300
```

-continued

```
acacccgcca acacccgctg acgcgccctg acgggcttgt ctgctcccgg catccgctta    360
cagacaagct gtgaccgtct ccgggagctg catgtgtcag aggttttcac cgtcatcacc    420
gaaacgcgcg agacgaaagg gcctcgtgat acgcctattt ttataggtta atgtcatgat    480
aataatggtt tcttagacgt caggtggcac ttttcgggga aatgtgcgcg gaacccctat    540
ttgtttattt ttctaaatac attcaaatat gtatccgctc atgagacaat aaccctgata    600
aatgcttcaa taatattgaa aaaggaagag tatgagtatt caacatttcc gtgtcgccct    660
tattcccttt tttgcggcat tttgccttcc tgtttttgct cacccagaaa cgctggtgaa    720
agtaaaagat gctgaagatc agttgggtgc acgagtgggt tacatcgaac tggatctcaa    780
cagcggtaag atccttgaga gttttcgccc cgaagaacgt tttccaatga tgagcacttt    840
taaagttctg ctatgtggcg cggtattatc ccgtattgac gccgggcaag agcaactcgg    900
tcgccgcata cactattctc agaatgactt ggttgagtac tcaccagtca cagaaaagca    960
tcttacggat ggcatgacag taagagaatt atgcagtgct gccataacca tgagtgataa   1020
cactgcggcc aacttacttc tgacaacgat cggaggaccg aaggagctaa ccgctttttt   1080
gcacaacatg ggggatcatg taactcgcct tgatcgttgg gaaccggagc tgaatgaagc   1140
cataccaaac gacgagcgtg acaccacgat gcctgtagca atgccaacaa cgttgcgcaa   1200
actattaact ggcgaactac ttactctagc ttcccggcaa caattaatag actggatgga   1260
ggcggataaa gttgcaggac cacttctgcg ctcggccctt ccggctggct ggtttattgc   1320
tgataaatct ggagccggtg agcgtgggtc tcgcggtatc attgcagcac tggggccaga   1380
tggtaagccc tcccgtatcg tagttatcta cacgacgggg agtcaggcaa ctatggatga   1440
acgaaataga cagatcgctg agataggtgc ctcactgatt aagcattggt aactgtcaga   1500
ccaagtttac tcatatatac tttagattga tttaaaactt catttttaat ttaaaaggat   1560
ctaggtgaag atcctttttg ataatctcat gaccaaaatc ccttaacgtg agttttcgtt   1620
ccactgagcg tcagaccccg tagaaaagat caaaggatct tcttgagatc cttttttct    1680
gcgcgtaatc tgctgcttgc aaacaaaaaa accaccgcta ccagcggtgg tttgtttgcc   1740
ggatcaagag ctaccaactc tttttccgaa ggtaactggc ttcagcagag cgcagatacc   1800
aaatactgtc cttctagtgt agccgtagtt aggccaccac ttcaagaact ctgtagcacc   1860
gcctacatac ctcgctctgc taatcctgtt accagtggct gctgccagtg gcgataagtc   1920
gtgtcttacc gggttggact caagacgata gttaccggat aaggcgcagc ggtcgggctg   1980
aacggggggt tcgtgcacac agcccagctt ggagcgaacg acctacaccg aactgagata   2040
cctacagcgt gagctatgag aaagcgccac gcttcccgaa gggagaaagg cggacaggta   2100
tccggtaagc ggcagggtcg gaacaggaga gcgcacgagg gagcttccag ggggaaacgc   2160
ctggtatctt tatagtcctg tcgggtttcg ccacctctga cttgagcgtc gatttttgtg   2220
atgctcgtca ggggggcgga gcctatcgaa aaacgccagc aacgcggcct ttttacggtt   2280
cctggccttt tgctggcctt ttgctcacat gttctttcct gcgttatccc ctgattctgt   2340
ggataaccgt attaccgcct ttgagtgagc tgataccgct cgccgcagcc gaacgaccga   2400
gcgcagcgag tcagtgagcg aggaagcgga agagcgccca atacgcaaac cgcctctccc   2460
cgcgcgttgg ccgattcatt aatgcagctg gcacgacagg tttcccgact cgaaagcggg   2520
cagtgagcgc aacgcaatta atgtgagtta gctcactcat taggcacccc aggctttaca   2580
ctttatgctt ccggctcgta tgttgtgtgg aattgtgagc ggataacaat ttcacacagg   2640
```

-continued aaacagctat gaccatgatt acgccaagct 2670

<210> SEQ ID NO 12
<211> LENGTH: 171
<212> TYPE: DNA
<213> ORGANISM: Artificial Sequence
<220> FEATURE:
<223> OTHER INFORMATION: Synthetic Polynucleotide

<400> SEQUENCE: 12
ggagacaagc uuauggcacc caggaagcaa cuggcuacaa aagccgcucg caugagugcg 60
cccucuacug gaggggugaa gaaaccucau uaagaauucu uaauuaaaaa aaaaaaaaaa 120
aaaaaaaaaa aaaaaaaaaa aaaaaaaaaa aaaaaaaaaa aaaaaaacua g 171

<210> SEQ ID NO 13
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 13

Met Ala Pro Arg Lys Gln Leu Ala Thr Lys Ala Ala Arg Met Ser Ala
1 5 10 15

Pro Ser Thr Gly Gly Val Lys Lys Pro His
20 25

<210> SEQ ID NO 14
<211> LENGTH: 81
<212> TYPE: DNA
<213> ORGANISM: Artificial Sequence
<220> FEATURE:
<223> OTHER INFORMATION: Synthetic Polynucleotide

<400> SEQUENCE: 14
auggcaccca ggaagcaacu ggcuacaaaa gccgcucgca ugagugcgcc cucuacugga 60
ggggugaaga aaccucauua a 81

<210> SEQ ID NO 15
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 15

Arg Lys Gln Leu Ala Thr Lys Ala Ala Arg Met Ser Ala Pro Ser Thr
1 5 10 15

Gly Gly Val Lys Lys
20

<210> SEQ ID NO 16
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 16

Met Ser Ala Pro Ser
1 5

<210> SEQ ID NO 17

```
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 17

Arg Met Ser Ala Pro
1               5


<210> SEQ ID NO 18
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 18

Ala Arg Met Ser Ala
1               5


<210> SEQ ID NO 19
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 19

Ala Ala Arg Met Ser
1               5


<210> SEQ ID NO 20
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 20

Lys Ala Ala Arg Met
1               5


<210> SEQ ID NO 21
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 21

aggaagcaac uggcuacaaa agccgcucgc augagugcgc ccucuacugg aggggugaag     60

aaa                                                                   63


<210> SEQ ID NO 22
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 22

Arg Lys Gln Leu Ala Thr Lys Ala Ala Arg Met Ser Ala Pro Ser Thr
1               5                   10                  15

Gly Gly Val Lys Lys Pro
            20
```

<210> SEQ ID NO 23
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 23

```
Gly Lys Ala Pro Arg Lys Gln Leu Ala Thr Lys Ala Ala Arg Met Ser
1               5                   10                  15

Ala Pro Ser Thr Gly Gly Val Lys Lys Pro His Arg Tyr
            20                  25
```

<210> SEQ ID NO 24
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 24

```
Gly Lys Ala Pro Arg Lys Gln Leu Ala Thr Lys Ala Ala Arg Met
1               5                   10                  15
```

<210> SEQ ID NO 25
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 25

```
Lys Ala Pro Arg Lys Gln Leu Ala Thr Lys Ala Ala Arg Met Ser
1               5                   10                  15
```

<210> SEQ ID NO 26
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 26

```
Ala Pro Arg Lys Gln Leu Ala Thr Lys Ala Ala Arg Met Ser Ala
1               5                   10                  15
```

<210> SEQ ID NO 27
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 27

```
Pro Arg Lys Gln Leu Ala Thr Lys Ala Ala Arg Met Ser Ala Pro
1               5                   10                  15
```

<210> SEQ ID NO 28
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 28

-continued

Arg Lys Gln Leu Ala Thr Lys Ala Ala Arg Met Ser Ala Pro Ser
1 5 10 15

<210> SEQ ID NO 29
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 29

Lys Gln Leu Ala Thr Lys Ala Ala Arg Met Ser Ala Pro Ser Thr
1 5 10 15

<210> SEQ ID NO 30
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 30

Gln Leu Ala Thr Lys Ala Ala Arg Met Ser Ala Pro Ser Thr Gly
1 5 10 15

<210> SEQ ID NO 31
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 31

Leu Ala Thr Lys Ala Ala Arg Met Ser Ala Pro Ser Thr Gly Gly
1 5 10 15

<210> SEQ ID NO 32
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 32

Ala Thr Lys Ala Ala Arg Met Ser Ala Pro Ser Thr Gly Gly Val
1 5 10 15

<210> SEQ ID NO 33
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 33

Thr Lys Ala Ala Arg Met Ser Ala Pro Ser Thr Gly Gly Val Lys
1 5 10 15

<210> SEQ ID NO 34
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 34

Lys Ala Ala Arg Met Ser Ala Pro Ser Thr Gly Gly Val Lys Lys 1 5 10 15

<210> SEQ ID NO 35
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 35

Ala Ala Arg Met Ser Ala Pro Ser Thr Gly Gly Val Lys Lys Pro
1 5 10 15

<210> SEQ ID NO 36
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 36

Ala Arg Met Ser Ala Pro Ser Thr Gly Gly Val Lys Lys Pro His
1 5 10 15

<210> SEQ ID NO 37
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 37

Arg Met Ser Ala Pro Ser Thr Gly Gly Val Lys Lys Pro His Arg
1 5 10 15

<210> SEQ ID NO 38
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 38

Met Ser Ala Pro Ser Thr Gly Gly Val Lys Lys Pro His Arg Tyr
1 5 10 15

<210> SEQ ID NO 39
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 39

Arg Lys Gln Leu Ala Thr Lys Ala Ala
1 5

<210> SEQ ID NO 40
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 40

Leu Ala Thr Lys Ala Ala Arg Met Ser
1 5

-continued

```
<210> SEQ ID NO 41
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 41

Ala Arg Met Ser Ala Pro Ser Thr Gly
1               5


<210> SEQ ID NO 42
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 42

Ser Ala Pro Ser Thr Gly Gly Val Lys
1               5
```

COMPOSITIONS FOR TREATMENT OF DIFFUSE INTRINSIC PONTINE GLIOMA

CROSS-REFERENCE TO RELATED APPLICATIONS

This application is a national phase application under 35 U.S.C. § 371 of International Application No. PCT/US2020/031096, filed May 1, 2020, which claims priority to U.S. Provisional Patent Application No. 62/842,525, filed May 2, 2019, the entire contents of which are incorporated herein by reference.

GRANT FUNDING DISCLOSURE

This invention was made with government support under grant number W81XWH-17-1-0510, awarded by the United States Army Research Acquisition Activity. The government has certain rights in the invention.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 29,178 byte ASCII (Text) file named "54160_Seqlisting.txt"; created on May 1, 2020.

BACKGROUND

Diffuse Intrinsic Pontine Glioma (DIPG) is an infiltrative and diffuse tumor found in the brain of pediatric patients. The median overall survival is 10-11 months and the 2-year survival rate is less than 10%. DIPG represents 10% to 20% of all pediatric brain cancer cases and is the number one cause of brain tumor-related deaths in children. Even when a diagnosed child survives past one year, they suffer from major neurological defects, as the growing tumor impinges on critical white matter tracts and local cranial nerve foci, leading to the onset of severe symptoms including ataxia, cranial nerve palsies, and long tract signs.

Treatment modalities for DIPG are limited. Because of its location and diffuse nature, DIPG cannot be addressed by surgical resection. Chemotherapies providing a therapeutic effect are few and far between. From 1984 to 2014, over 65 clinical trials using adjuvant chemotherapeutic agents have failed to demonstrate a therapeutic effect in patients with DIPG. While corticosteroids offer some relief by way of reducing peritumoral edema, this treatment does not improve the outcome of the DIPG patients. Not surprisingly, the 5-year survival rate of DIPG-diagnosed patients have remained essentially the same since 1962.

In view of the foregoing, there is a need for improved methods of treating DIPG.

SUMMARY

Presented herein for the first time are data which shows an increase in central memory T cells having antigen-specificity for a mutant Histone H3 protein comprising a K27M mutation upon administration of a liposome comprising RNA molecules encoding an MHC Class II epitope (and optionally at least one MHC Class I epitope) of the mutant Histone H3 protein comprising the K27M mutation. Accordingly, the present disclosure provides compositions comprising a liposome comprising ribonucleic acid (RNA) molecules and a cationic lipid, wherein the RNA molecules encode at least one MHC Class II epitope (and optionally at least one MHC Class I epitope) of a mutant Histone 3 (H3) protein comprising a K27M mutation. In exemplary embodiments, the MHC Class II epitope comprises at least 5-10 consecutive amino acids of the sequence of MAPRKQLATKAARMSAPSTGGVKKPH (SEQ ID NO: 13) or RKQLATKAARMSAPSTGGVKK (SEQ ID NO: 15). In exemplary aspects, the MHC Class II epitope comprises at least 11-17 or at least 18-21 consecutive amino acids of the sequence of SEQ ID NO: 13 or SEQ ID NO: 15. In various instances, the MHC Class II epitope comprises at least 22-25 consecutive amino acids of the sequence of SEQ ID NO: 13 or SEQ ID NO: 15. In exemplary aspects, the MHC Class II epitope comprises the amino acid sequence of SEQ ID NO: 13 or SEQ ID NO: 15. In various aspects, the MHC Class II epitope comprises the sequence of ARM, RMS, or MSA. Optionally, the MHC Class II epitope comprises the sequence of MSAPS (SEQ ID NO: 16), RMSAP (SEQ ID NO: 17), ARMSA (SEQ ID NO: 18), AARMS (SEQ ID NO: 19), or KAARM (SEQ ID NO: 20). In exemplary aspects, the RNA molecules comprise at least a portion of the nucleotide sequence of SEQ ID NO: 12 which encodes the MHC Class II epitope. In some aspects, the RNA molecules comprise the nucleotide sequence of SEQ ID NO: 14 or SEQ ID NO: 21. Optionally, the RNA molecules comprise the nucleotide sequence of SEQ ID NO: 12.

In some aspects, the liposome comprises the cationic lipid, DOTAP. In some aspects, the liposome (a) has a zeta potential of about 30 mV to about 60 mV, optionally, about 40 mV to about 50 mV, (b) is about 50 nm to about 250 nm in diameter, optionally, about 70 nm to about 200 nm in diameter, (c) or a combination thereof. In various aspects, the composition comprises a plurality of liposomes, each liposome of which is about 50 nm to about 250 nm in diameter, optionally, about 70 nm to about 200 nm in diameter. The RNA molecules in some instances are complexed with the cationic lipid via electrostatic interactions. Optionally, the liposomes are prepared by mixing the RNA molecules and the cationic lipid at a RNA:cationic lipid ratio of about 1 to about 10 to about 1 to about 20, optionally, about 1 to about 15. In various aspects, the composition comprises about $10^{10}$ liposomes per mL to about $10^{15}$ liposomes per mL, optionally about $10^{12}$ liposomes±10% per mL. In exemplary instances, the RNA molecules are mRNA and in exemplary aspects, each RNA molecule comprises a 5'-cap. In certain instances, the composition further comprises lysosome-associated membrane proteins (LAMPs). In exemplary aspects, the RNA molecules further encode a lysosome-associated membrane protein (LAMP). In various aspects, the RNA molecules encode a chimeric protein comprising a LAMP protein and the MHC Class II epitope of the mutant H3 protein and optionally at least one MHC Class I epitope.

The present disclosure also provides methods of generating a liposome comprising ribonucleic acid (RNA) molecules and a cationic lipid, wherein the RNA molecules encode at least one MHC Class II epitope (and optionally at least one MHC Class I epitope) of a mutant Histone 3 (H3) protein comprising a K27M mutation. In exemplary embodiments, the method comprises (i) in vitro transcribing a nucleic acid comprising a nucleotide sequence encoding the RNA molecules, (ii) chemically adding a 5'-cap to the in vitro transcribed RNA molecules, and (iii) mixing the RNA molecules comprising the 5'-cap with a cationic lipid. In exemplary aspects, the cationic lipid is DOTAP and/or the RNA molecules and cationic lipid are mixed at a RNA:lipid ratio of about 1 to about 10 to about 1 to about 20 (e.g., about 1 to about 15). In various aspects, the nucleotide sequence encoding the RNA molecules comprises the sequence of SEQ ID NO: 11 and optionally the nucleotide sequence encoding the RNA molecules is operably linked to a promoter, optionally a T7 promoter. In various aspects, the nucleotide sequence encoding the RNA molecules is flanked by a 5' untranslated region (5'UTR) and a 3' untranslated region (3'UTR). In some aspects, the nucleic acid comprises a sequence encoding a polyA tail. Optionally, the nucleic acid is a linearized plasmid (e.g., linearized DNA). Further provided are liposomes generated by the presently disclosed method of generating a liposome. In various instances, the liposome is formulated for intravenous injection.

RNA molecules encoding an MHC Class II epitope (and optionally at least one MHC Class I epitope) of a mutant Histone 3 (H3) protein comprising a K27M mutation are further provided herein. In exemplary embodiments, the MHC Class II epitope comprises at least 5-10 consecutive amino acids of the sequence of MAPRKQLATKAARMSAPSTGGVKKPH (SEQ ID NO: 13) or RKQLATKAARMSAPSTGGVKK (SEQ ID NO: 15). In various aspects, the MHC Class II epitope comprises at least 11-17 consecutive amino acids of the sequence of SEQ ID NO: 13 or SEQ ID NO: 15. In various instances, the MHC Class II epitope comprises at least 18-21 consecutive amino acids of the sequence of SEQ ID NO: 13 or SEQ ID NO: 15. In certain aspects, the MHC Class II epitope comprises at least 11-25 consecutive amino acids of the sequence of SEQ ID NO: 13 or SEQ ID NO: 15. In exemplary aspects, the MHC Class II epitope comprises at least 11-17 consecutive amino acids of the sequence of SEQ ID NO: 13 or SEQ ID NO: 15. In exemplary instances, the MHC Class II epitope comprises the sequence of SEQ ID NO: 13 or SEQ ID NO: 15. In various aspects, the MHC Class II epitope comprises the sequence of ARM, RMS, or MSA, optionally, wherein the MHC Class II epitope comprises the sequence of MSAPS (SEQ ID NO: 16), RMSAP (SEQ ID NO: 17), ARMSA (SEQ ID NO: 18), AARMS (SEQ ID NO: 19), or KAARM (SEQ ID NO: 20). In certain instances, the RNA molecule comprises at least a portion of the nucleotide sequence of SEQ ID NO: 12 which encodes the MHC Class II epitope, optionally, the RNA molecule comprises the nucleotide sequence of SEQ ID NO: 14 or SEQ ID NO: 21 or SEQ ID NO: 12. In exemplary instances, the RNA molecule further comprises a 5' cap and/or a polyA tail and/or a nucleotide sequence encoding a lysosome-associated membrane protein (LAMP), optionally, wherein the RNA molecule encodes a chimeric protein comprising a LAMP protein and the MHC Class II epitope of the mutant H3 protein. Nucleic acids comprising a nucleotide sequence encoding the RNA molecule of the present disclosure are further provided herein. Compositions, e.g., pharmaceutical compositions, comprising the presently disclosed liposome, RNA molecule or nucleic acid, or a combination thereof, are additionally provided herein.

Methods of increasing in a subject the number of central memory T cells having antigen specificity for an epitope of a mutant Histone 3 (H3) protein comprising a K27M mutation are provided by the present disclosure. In exemplary embodiments, the method comprises administering to the subject a composition comprising the presently disclosed liposome, RNA molecule or nucleic acid, or a combination thereof, in an amount effective to increase the central memory T cells in the subject. Also, methods of enhancing in a subject an immune response against a diffuse midline glioma (DMG) expressing a mutant Histone 3 (H3) protein comprising a K27M mutation are provided. In exemplary embodiments, the method comprises administering to the subject a composition comprising the presently disclosed liposome, RNA molecule or nucleic acid, or a combination thereof, in an amount effective to increase the an immune response against the DMG in the subject. In exemplary aspects, the subject has a diffuse midline glioma (DMG) expressing a mutant Histone 3 (H3) protein comprising a K27M mutation or a predisposition to having the DMG. In various aspects, the subject has been treated for a DMG is in remission for the DMG. Methods of treating a subject with a diffuse midline glioma (DMG) expressing a mutant Histone 3 (H3) protein comprising a K27M mutation are also provided herein. In exemplary embodiments, the method comprises administering to the subject a presently disclosed composition in an amount effective to treat the DMG in the subject. In various aspects, the composition is systemically administered to the subject. In various aspects, the composition is intravenously administered to the subject.

In some aspects, the method comprises administering to the subject the composition or liposome once a week. Optionally, the DMG is diffuse intrinsic pontine glioma (DIPG) and/or the subject is age 17 years or less. In various instances, the method further comprises administering to the subject one or more lysosome-associated membrane proteins (LAMPs), as further described herein.

BRIEF DESCRIPTION OF THE DRAWINGS

FIG. 1 is a schematic of a process of designing a peptide sequence predicted to contain MHC class II epitopes. Predictive screening to determine potential binders was performed using NetMHCII 2.3. Since the maximum input for peptide length prediction is 15-amino acids. Each sequential 15-mer encompassing the peptide was tested for potential binding (mak>5.0%) for all human HLA class II alleles available on the prediction platform.

FIG. 5A is a graph of % of mice surviving for the number of days post tumor implantation of untreated mice, mice treated with NPs alone, or mice treated with NPs complexed with RNA encoding a strong binding MHC Class I epitope. The treatment administration schedules in 5A-5E are outlined in 3A. While a MHC class I driven immunogenic response prolongs survival it does not produce robust long-term survivors.

FIG. 5B is a graph of % of mice surviving for the number of days post tumor implantation of untreated mice or mice treated with NPs complexed with RNA encoding MHC Class I- and Class II-restricted epitopes. With the inclusion of MHC class II alongside MHC class I, a robust survivorship outcome is accomplished in tumor-mRNA-NP treated mice.

FIG. 5C is a pair of graphs demonstrating the % of antigen specific CD8+ splenocytes (left) or % of cells expressing IFNγ (right) of untreated mice or mice treated with RNA alone, irrelevant RNA containing NPs (CFA-OVA), or tumor relevant RNA NPs. NP encapsulated RNA encoding MHC presenting peptides drives antigen-specific immunity and leads to a functional antigen-specific lymphocyte population.

FIG. 5D is a graph of the % of CD11c+CD86+ cells of untreated mice or mice treated with GFP RNA-NPs or total tumor mRNA NPs. Total tumor mRNA-NP treated mice show greater activation of antigen presenting dendritic cells relative to NP-alone or irrelevant-NP (GFP) treated mice.

FIG. 5E is a graph of the % of CD62+CD44+ CD3+ cells of untreated mice or mice treated with GFP RNA-NPs or total tumor mRNA NPs. Administration of total tumor mRNA-NPs leads to expansion of the T cell central memory compartment relative to controls.

DETAILED DESCRIPTION

Nucleic Acid Molecules

Figure 2:
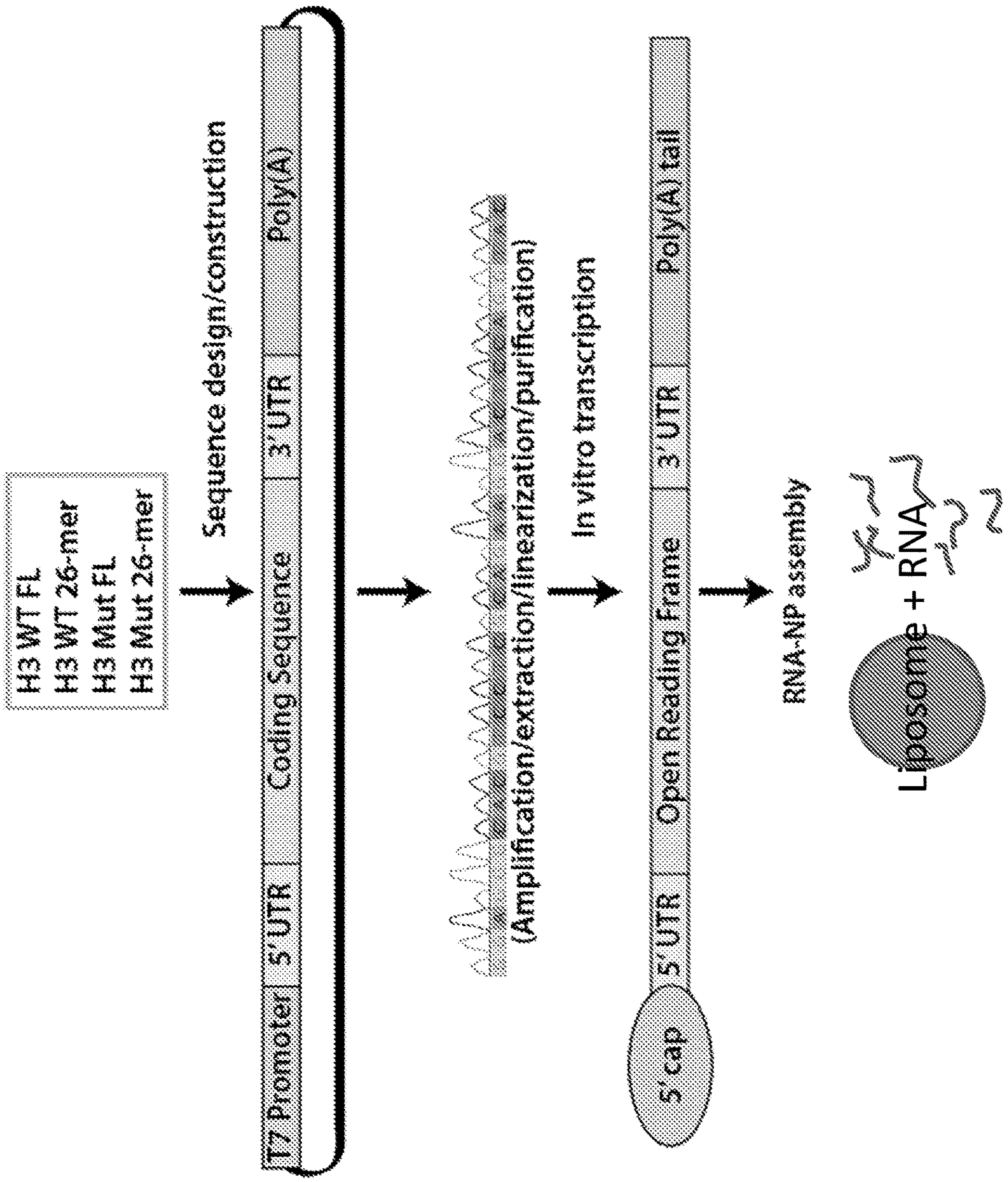
FIG. 2 is a schematic of a process of preparing RNA molecules from *E. coli*-amplified, linearized plasmid DNA via in vitro transcription (IVT). The chosen sequences were placed into a plasmid containing a T7 promoter, a 5' and 3' untranslated region (UTR) and an incorporated poly (A) tail. Plasmids containing the coding sequence (CDS) of interest were amplified in *E. coli* and extracted with a commercial plasmid preparation kit. Following confirmation of the sequence, plasmids were linearized and mRNA is created through 5' cap addition and in vitro transcription. The RNA molecules are then used in RNA-NP assembly.

The present disclosure provides a nucleic acid molecule comprising a nucleotide sequence encoding at least one MHC Class II epitope of a mutant Histone 3 (H3) protein comprising a K27M mutation. By "nucleic acid molecule" as used herein includes "polynucleotide" and "oligonucleotide" and generally means a polymer of deoxyribonucleic acid (DNA) or ribonucleic acid (RNA), which can be single-stranded or double-stranded, synthesized or obtained (e.g., isolated and/or purified) from natural sources, which can contain natural, non-natural or altered nucleotides, and which can contain a natural, non-natural or altered internucleotide linkage. In exemplary aspects, the nucleic acid molecule comprises one or more modified nucleotides, such as, e.g., 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridme, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, N-substituted adenine, 7-methylguanine, 5-methylammomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouratil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. In exemplary aspects, the nucleic acid molecule comprises one or more non-natural or altered internucleotide linkages, such as a phosphoroamidate linkage or a phosphorothioate linkage, in place of the phosphodiester linkage found between the nucleotides of a naturally-occurring DNA molecule or RNA molecule. In exemplary aspects, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

In exemplary embodiments, the nucleic acid molecule is an RNA molecule and in some aspects, the RNA molecule is a mature mRNA or a processed mRNA that lacks introns. In exemplary aspects, the RNA molecule comprises a 5' cap, a poly(A) tail, or a combination of both. The 5' cap in various aspects comprises a 7-methylguanylate and is attached to the 5' end of the RNA molecule via a 5' to 5' triphosphate linkage. In various aspects, the 5' cap is added to the RNA molecule via a chemical addition reaction.

In exemplary embodiments, the nucleic acid molecules are constructed based on chemical synthesis and/or enzymatic ligation reactions using procedures known in the art. See, for example, Sambrook et al., supra, and Ausubel et al., supra. In various aspects, the RNA molecules are produced outside of a cell via in vitro transcription techniques. In various aspects, the RNA molecules are synthetic RNA molecules produced by in vitro transcription. Further descriptions of exemplary methods of making the RNA molecules are provided below.

The presently disclosed nucleic acid molecules (e.g., RNA molecules) comprise a nucleotide sequence encoding at least one MHC Class II epitope of a mutant Histone 3 (H3) protein comprising a K27M mutation. By "MHC Class II epitope" refers to a portion of a protein or peptide that binds to a Major Histocompatibility Complex (MHC) Class II molecule. The MHC Class II epitope in various aspects is about 10 to about 30 amino acids long, optionally about 15 to about 24 amino acids long. In various instances, the MHC Class II epitope is about 10 to about 25 amino acids long or about 10 to about 20 amino acids long or about 15 to 30 amino acids long or about 15 to 25 amino acids long. In various aspects, due to the antigen binding groove of MHC Class II molecules having two open ends, only a portion of the MHC Class II epitope actually contacts the antigen binding groove of the MHC Class II molecule, while remaining portions of the epitope do not contact the antigen binding groove.

In exemplary aspects, the MHC Class II epitope binds to a human MHC Class II molecule. In exemplary aspects, the human MHC Class II molecule is an HLA-DP, HLA-DM, HLA-DOA, HLA-DOB, HLA-DQ, and HLA-DR. The amino acid sequences of MHC Class II molecules are known in the art and are available in the NCBI Protein database as shown in Table A.

TABLE A

| Official Symbol | NCBI Gene ID | NCBI mRNA Accession No(s). | NCBI Protein Accession No(s). |
|---|---|---|---|
| HLA-DMA | 3108 | NM_006120.3 | NP_006111.2 |
| HLA-DMB | 3109 | NM_002118.4 | NP_002109.2 |
| HLA-DOA | 3111 | NM_002119.3 | NP_002110.1 |
| HLA-DOB | 3112 | NM_002120.3 | NP_002111.1 |
| HLA-DPA1 | 3113 | NM_00124524.1 | NP_001229453.1 |
| | | NM_0012452525.1 | NP_001229454.1 |
| | | NM_033554.3 | NP_291032.2 |
| HLA-DPB1 | 3115 | NM_002121.5 | NP_002112.3 |
| HLA-DQA1 | 3117 | NM_002122.3 | NP_002113.2 |
| HLA-DQA2 | 3118 | NM_020056.4 | NP_064440.1 |
| HLA-DQB1 | 3119 | NM_001243961.1 | NP_001230890.1 |
| | | NM_001243962.1 | NP_001230891.1 |
| | | NM_002123.4 | NP_002114.3 |
| HLA-DQB2 | 3120 | NM_001198858.1 | NP_001185787.1 |
| | | NM_001300790.1 | NP_001287719.1 |
| HLA-DRA | 3122 | NM_019111.4 | NP_061984.2 |
| HLA-DRB1 | 3123 | NM_01243965.1 | NP_001230894.1 |
| | | NM_002124.3 | NP_002115.2 |
| HLA-DRB3 | 3125 | NM_022555.3 | NP_072049.2 |
| HLA-DRB4 | 3126 | NM_021983.4 | NP_068818.4 |
| HLA-DRB5 | 3127 | NM_002125.3 | NP_002116.2 |

The mutant H3 protein in various instances is the H3.3 protein encoded by the H3F3A gene comprising a Lys to Met mutation at amino acid position 27 or is the H3.1 protein encoded by the HIST1H3B gene comprising a Lys to Met mutation at amino acid position 27. SEQ ID NO: 1 provides the amino acid sequence of the H3.3 protein comprising the K27M mutation. In exemplary aspects, the MHC Class II epitope comprises at least 5-10 consecutive amino acids of MAPRKQLATKAARMSAPSTGGVKKPH (SEQ ID NO: 13) or RKQLATKAARMSAPSTGGVKK (SEQ ID NO: 15). In various instances, the MHC Class II epitope comprises at least 11-17 consecutive amino acids of the sequence of SEQ ID NO: 13 or SEQ ID NO: 15. In certain instances, the MHC Class II epitope comprises at least 18-21 consecutive amino acids of the sequence of SEQ ID NO: 13 or SEQ ID NO: 15. In exemplary aspects, the MHC Class II epitope comprises at least 22-25 consecutive amino acids of the sequence of SEQ ID NO: 13 or SEQ ID NO: 15. In certain instances, the MHC Class II epitope comprises the sequence of SEQ ID NO: 13 or SEQ ID NO: 15. With regard to the RNA molecules of the presently disclosed liposomes, the MHC Class II epitope comprises the sequence of ARM, RMS, or MSA, optionally, wherein the MHC Class II epitope comprises the sequence of MSAPS (SEQ ID NO: 16), RMSAP (SEQ ID NO: 17), ARMSA (SEQ ID NO: 18), AARMS (SEQ ID NO: 19), or KAARM (SEQ ID NO: 20). In exemplary instances, the RNA molecules comprise at least a portion of the nucleotide sequence of SEQ ID NO: 12 which encodes the MHC Class II epitope. In some aspects, the RNA molecules comprises the nucleotide sequence of SEQ ID NO: 14 or SEQ ID NO: 21. In exemplary aspects, the RNA molecules comprise the nucleotide sequence of SEQ ID NO: 12.

In various instances, the presently disclosed nucleic acid molecules (e.g., RNA molecules) comprise a nucleotide sequence encoding at least 2, at least 3, at least 4, or at least 5 MHC Class II epitopes of a mutant Histone 3 (H3) protein comprising a K27M mutation. In exemplary instances, the presently disclosed nucleic acid molecules (e.g., RNA molecules) comprise a nucleotide sequence encoding at least 6, at least 7, at least 8, at least 9, or at least 10 MHC Class II epitopes of a mutant Histone 3 (H3) protein comprising a K27M mutation. In exemplary aspects, the presently disclosed nucleic acid molecules (e.g., RNA molecules) comprise a nucleotide sequence encoding 10 or more MHC Class II epitopes, e.g., 11, 12, 13, 14, 15, 16, 17, 18, 19, or 20 MHC Class II epitopes, of a mutant Histone 3 (H3) protein comprising a K27M mutation.

In various aspects, the presently disclosed nucleic acid molecules (e.g., RNA molecules) comprise a nucleotide sequence encoding at least one MHC Class II epitope of a mutant Histone 3 (H3) protein comprising a K27M mutation and at least one MHC Class I epitope of the mutant H3 protein comprising the K27M mutation. By "MHC Class I epitope" refers to a portion of a protein or peptide that binds to a Major Histocompatibility Complex (MHC) Class I molecule. In exemplary aspects, the MHC Class I epitope binds to a human MHC Class I molecule. In exemplary aspects, the human MHC Class I molecule is an HLA-A, HLA-B, HLA-C, HLA-E, HLA-F, and HLA-G. The MHC Class I epitope in various aspects is about 6 to about 12 amino acids long, optionally about 8 to about 12 amino acids long. In various instances, the MHC Class I epitope is about 6 to about 10 amino acids long or about 6 to about 8 amino acids long or about 8 to 12 amino acids long or about 10 to 12 amino acids long. In exemplary aspects, the MHC Class I epitope comprises at least 6, 7, 8, 9, 10, 11, or 12 consecutive amino acids of MAPRKQLATKAARMSAPSTGGVKKPH (SEQ ID NO: 13) or RKQLATKAARMSAPSTGGVKK (SEQ ID NO: 15). With regard to the RNA molecules of the presently disclosed liposomes, the MHC Class I epitope comprises the sequence of ARM, RMS, or MSA, optionally, wherein the MHC Class II epitope comprises the sequence of MSAPS (SEQ ID NO: 16), RMSAP (SEQ ID NO: 17), ARMSA (SEQ ID NO: 18), AARMS (SEQ ID NO: 19), or KAARM (SEQ ID NO: 20). In various aspects, the RNA comprising a sequence encoding an amino acid sequence of any one SEQ ID NOs: 28-35 or any one of SEQ ID NOs: 39-42. In exemplary instances, the RNA molecules comprise at least a portion of the nucleotide sequence of SEQ ID NO: 12 which encodes the MHC Class I epitope. In some aspects, the RNA molecules comprises the nucleotide sequence of SEQ ID NO: 14 or SEQ ID NO: 21. In exemplary aspects, the RNA molecules comprise the nucleotide sequence of SEQ ID NO: 12. In various aspects, the presently disclosed nucleic acid molecules (e.g., RNA molecules) comprise a nucleotide sequence encoding at least one (e.g., at least 2, at least 3, at least 4, at least 5, at least 6, at least 7, at least 8, at least 9, at least 10, or more) MHC Class II epitope(s) and at least one (e.g., at least 2, at least 3, at least 4, at least 5, at least 6, at least 7, at least 8, at least 9, at least 10, or more) MHC Class I epitope of the mutant H3 protein comprising the K27M mutation. In various aspects, the presently disclosed nucleic acid molecules (e.g., RNA molecules) comprise a nucleotide sequence encoding multiple MHC Class II epitopes and multiple MHC Class I epitopes. In exemplary aspects, the RNA molecule encodes a peptide that binds to at least 2, at least 3, at least 4, at least 5, at least 6, at least 7, at least 8, at least 9, at least 10, at least 11, at least 12, at least 13, at least 14, at least 15, or more different HLA molecules. In exemplary aspects, the RNA molecule encodes a peptide that binds to at least 2, at least 3, at least 4, at least 5, at least 6, at least 7, at least 8, at least 9, at least 10, at least 11, at least 12, at least 13, at least 14, at least 15, or more different human Class II molecules, and/or at least 2, at least 3, at least 4, at least 5, at least 6, at least 7, at least 8, at least 9, at least 10, at least 11, at least 12, at least 13, at least 14, at least 15, or more different human Class I molecules. With being bound to a particular theory, the RNA encoding multiple MHC Class I and Class II epitopes advantageously allow it to be used in many different subjects to elicit an immune response against the mutant H3 protein.

In various instances, the presently disclosed nucleic acid molecules (e.g., RNA molecules) comprise a nucleotide sequence encoding at least one MHC Class II epitope of a mutant Histone 3 (H3) protein comprising a K27M mutation, optionally, at least one MHC Class I epitope of the mutant H3 protein, and another nucleotide sequence. In various aspects, the other nucleotide sequence encodes another epitope or another polypeptide. In exemplary aspects, the RNA molecule further comprises a nucleotide sequence encoding a lysosome-associated membrane protein (LAMP). LAMPs are membrane proteins specific to lysoomes comprising homologous lysosome-luminal domains separated by a proline-rich hinge region, a transmembrane domain and a cytoplasmic domain. A review on LAMPs is provided at Schwake et al., Traffic (2013) http://koi.org/10.1111/tra.12056. In various aspects, the nucleic acid molecule (e.g., RNA molecule) comprising a nucleotide sequence encoding a chimeric protein comprising a LAMP protein and the MHC Class II epitope of the mutant H3 protein comprising a K27M mutation. In various aspects, the LAMP protein is located N-terminal to the MHC Class II epitope. In certain aspects, the LAMP protein is a LAMP1, LAMP 2, LAMP3, LAMP4, or LAMP5 protein. The sequences of such LAMP proteins are known in the art. For example, the mRNA sequence of the LAMP1 precursor is available as NCBI Accession No. NM_005561.4 and the amino acid sequence of LAMP1 precursor is available as NCBI Accession No. NP_005552.3. Also, for example, the mRNA sequence of the LAMP2 isoform C precursor is available as NCBI Accession No. NM_001122606.1 and the amino acid sequence of LAMP2 isoform C precursor is available as NCBI Accession No. NP_001116078.1. The mRNA sequence of the LAMP3 precursor is available as NCBI Accession No. NM_014398.4 and the amino acid sequence of LAMP3 precursor is available as NCBI Accession No. NP_055213.2.

In various aspects, the nucleic acid molecules are complexed with a cationic lipid to make a particle (e.g., nanoparticle) or liposome (e.g., nanoliposome). In various instances, the RNA molecules are complexed with the cationic lipid via electrostatic interactions. In exemplary aspects, the liposomes are prepared by mixing the RNA molecules and the cationic lipid at a RNA:cationic lipid ratio of about 1 to about 10 to about 1 to about 20, optionally, about 1 to about 15. Methods of making such particles and liposomes are provided herein. Compositions, e.g., pharmaceutical compositions, comprising the nucleic acid molecule (e.g., RNA molecule) or particle or liposome are provided herein. Further descriptions of the compositions are provided below.

Additionally provided by the present disclosure are nucleic acid molecules comprising a nucleotide sequence encoding the RNA molecule of the present disclosure. In exemplary aspects, the nucleic acid molecule comprises a nucleotide sequence encoding an RNA molecule comprising a nucleotide sequence encoding at least one MHC Class II epitope of a mutant Histone 3 (H3) protein comprising a K27M mutation and optionally at least one MHC Class I epitope of the mutant H3 protein. In exemplary aspects, the nucleic acid comprises DNA and the nucleic acid molecules comprise DNA encoding the RNA molecule encoding an MHC Class II epitope of a mutant Histone 3 (H3) protein comprising a K27M mutation, optionally, the nucleic acid molecules comprise DNA comprising a sequence of SEQ ID NO: 11. Compositions, e.g., pharmaceutical compositions, comprising the nucleic acid molecule (e.g., DNA encoding the RNA molecule) are further provided herein.

Liposomes

The present disclosure provides liposomes comprising ribonucleic acid (RNA) molecules and a cationic lipid, wherein the RNA molecules encode at least one MHC Class II epitope of a mutant Histone 3 (H3) protein comprising a K27M mutation, optionally, at least one MHC Class I epitope, and compositions (e.g., pharmaceutical compositions) comprising the liposomes.

Liposomes are artificially-prepared vesicles which, in exemplary aspects, are primarily composed of a lipid bilayer. Liposomes in various instances are used as a delivery vehicle for the administration of nutrients and pharmaceutical agents. In various aspects the liposomes of the present disclosure are of different sizes and the composition may comprise one or more of (a) a multilamellar vesicle (MLV) which may be hundreds of nanometers in diameter and may contain a series of concentric bilayers separated by narrow aqueous compartments, (b) a small unicellular vesicle (SUV) which may be smaller than 50 nm in diameter, and (c) a large unilamellar vesicle (LUV) which may be between 50 and 500 nm in diameter. Liposomes in various instances are designed to comprise opsonins or ligands in order to improve the attachment of liposomes to unhealthy tissue or to activate events such as, but not limited to, endocytosis. In exemplary aspects, liposomes contain a low or a high pH in order to improve the delivery of the pharmaceutical formulations. In various instances, liposomes are formulated depending on the physicochemical characteristics such as, but not limited to, the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimization size, polydispersity and the shelf-life of the vesicles for the intended application, and the batch-to-batch reproducibility and possibility of large-scale production of safe and efficient liposomal products.

In exemplary aspects, the liposome has a diameter within the nanometer range and accordingly in certain instances are referred to herein as "nanoliposomes" or "nanoparticles" (abbreviated as NPs). In exemplary aspects, the liposome has a diameter between about 50 nm to about 500 nm, e.g., about 50 nm to about 450 nm, about 50 nm to about 400 nm, about 50 nm to about 350 nm, about 50 nm to about 300 nm, about 50 nm to about 250 nm, about 50 nm to about 200 nm, about 50 nm to about 150 nm, about 50 nm to about 100 nm, about 100 nm to about 500 nm, about 150 nm to about 500 nm, about 200 nm to about 500 nm, about 250 nm to about 500 nm, about 300 nm to about 500 nm, about 350 nm to about 500 nm, about 400 nm to about 500 nm. In exemplary aspects, the liposome has a diameter between about 50 nm to about 300 nm, e.g., about 100 nm to about 250 nm, about 110 nm±5 nm, about 115 nm±5 nm, about 120 nm±5 nm, about 125 nm±5 nm, about 130 nm±5 nm, about 135 nm±5 nm, about 140 nm±5 nm, about 145 nm±5 nm, about 150 nm±5 nm, about 155 nm±5 nm, about 160 nm±5 nm, about 165 nm±5 nm, about 170 nm±5 nm, about 175 nm±5 nm, about 180 nm±5 nm, about 190 nm±5 nm, about 200 nm±5 nm, about 210 nm±5 nm, about 220 nm±5 nm, about 230 nm±5 nm, about 240 nm±5 nm, about 250 nm±5 nm, about 260 nm±5 nm, about 270 nm±5 nm, about 280 nm±5 nm, about 290 nm±5 nm, about 300 nm±5 nm. In exemplary aspects, the liposome is about 50 nm to about 250 nm in diameter. In some aspects, the liposome is about 70 nm to about 200 nm in diameter. In exemplary aspects, the composition comprises a heterogeneous mixture of liposomes ranging in diameter, e.g., about 50 nm to about 500 nm or about 50 nm to about 250 nm in diameter. Optionally, the composition comprises a heterogeneous mixture of liposomes ranging from about 70 nm to about 200 nm in diameter.

In exemplary aspects, the liposome has a zeta potential of about 30 mV to about 60 mV. In other words, in certain aspects, the liposome has an overall surface net charge of about 30 mV to about 60 mV (e.g., about 30 mV to about 55 mV, about 30 mV to about 50 mV, 30 mV to about 45 mV, about 30 mV to about 40 mV, about 30 mV to about 35 mV, about 35 mV to about 60 mV, about 40 mV to about 60 mV, about 45 mV to about 60 mV, about 50 mV to about 60 mV, or about 55 mV to about 60 mV. In exemplary aspects, the liposome has an overall surface net charge of about 40 mV to about 50 mV.

In exemplary embodiments, the liposomes comprise a cationic lipid. In some embodiments, the cationic lipid is a low molecular weight cationic lipid such as those described in U.S. Patent Application No. 20130090372, the contents of which are herein incorporated by reference in their entirety. The cationic lipid in exemplary instances is a cationic fatty acid, a cationic glycerolipid, a cationic glycerophospholipid, a cationic sphingolipid, a cationic sterol lipid, a cationic prenol lipid, a cationic saccharolipid, or a cationic polyketide. In exemplary aspects, the cationic lipid comprises two fatty acyl chains, each chain of which is independently saturated or unsaturated. In some instances, the cationic lipid is a diglyceride. For example, in some instances, the cationic lipid may be a cationic lipid of Formula I or Formula II:

[Formula I]

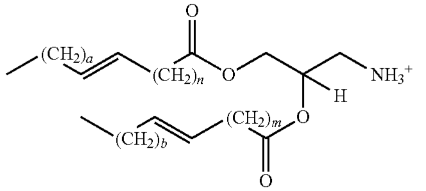

[Formula II]

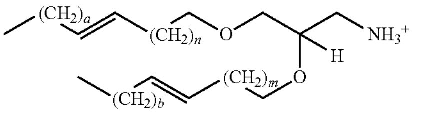

wherein each of a, b, n, and m is independently an integer between 2 and 12 (e.g., between 3 and 10). In some aspects, the cationic lipid is a cationic lipid of Formula I wherein each of a, b, n, and m is independently an integer selected from 3, 4, 5, 6, 7, 8, 9, and 10. In exemplary instances, the cationic lipid is DOTAP (1,2-dioleoyl-3-trimethylammonium-propane), or a derivative thereof. In exemplary instances, the cationic lipid is DOTMA (1,2-di-O-octadecenyl-3-trimethylammonium propane), or a derivative thereof.

In some embodiments, the liposomes are formed from 1,2-dioleyloxy-N,N-dimethylaminopropane (DODMA) liposomes, DiLa2 liposomes from Marina Biotech (Bothell, Wash.), 1,2-dilinoleyloxy-3-dimethylaminopropane (DLin-DMA), 2,2-dilinoleyl-4-(2-dimethylaminoethyl)-[1,3]-dioxolane (DLin-KC2-DMA), and MC3 (US20100324120; herein incorporated by reference in its entirety). In some embodiments, the liposomes are formed from the synthesis of stabilized plasmid-lipid particles (SPLP) or stabilized nucleic acid lipid particle (SNALP) that have been previously described and shown to be suitable for oligonucleotide delivery in vitro and in vivo. The liposomes in some aspects are composed of 3 to 4 lipid components in addition to the nucleic acid molecules. In exemplary aspects, the liposome comprises 55% cholesterol, 20% disteroylphosphatidyl choline (DSPC), 10% PEG-S-DSG, and 15% 1,2-dioleyloxy-N,N-dimethylaminopropane (DODMA), as described by Jeffs et al. In exemplary instances, the liposome comprises 48% cholesterol, 20% DSPC, 2% PEG-c-DMA, and 30% cationic lipid, where the cationic lipid can be 1,2-distearloxy-N,N-dimethylaminopropane (DSDMA), DODMA, DLin-DMA, or 1,2-dilinolenyloxy-3-dimethylaminopropane (DLenDMA), as described by Heyes et al.

In some embodiments, the liposomes comprise from about 25.0% cholesterol to about 40.0% cholesterol, from about 30.0% cholesterol to about 45.0% cholesterol, from about 35.0% cholesterol to about 50.0% cholesterol and/or from about 48.5% cholesterol to about 60% cholesterol. In some embodiments, the liposomes may comprise a percentage of cholesterol selected from the group consisting of 28.5%, 31.5%, 33.5%, 36.5%, 37.0%, 38.5%, 39.0% and 43.5%. In some embodiments, the liposomes may comprise from about 5.0% to about 10.0% DSPC and/or from about 7.0% to about 15.0% DSPC.

In some embodiments, the liposomes are DiLa2 liposomes (Marina Biotech, Bothell, Wash.), SMARTICLES® (Marina Biotech, Bothell, Wash.), neutral DOPC (1,2-dioleoyl-sn-glycero-3-phosphocholine) based liposomes (e.g., siRNA delivery for ovarian cancer (Landen et al. Cancer Biology & Therapy 2006 5(12)1708-1713); herein incorporated by reference in its entirety) and hyaluronan-coated liposomes (Quiet Therapeutics, Israel).

In various instances, the cationic lipid comprises 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino)butanoyl)oxy)heptadecanedioate (L319), and further comprise a neutral lipid, a sterol and a molecule capable of reducing particle aggregation, for example a PEG or PEG-modified lipid.

The liposome in various aspects comprises DLin-DMA, DLin-K-DMA, 98N12-5, C12-200, DLin-MC3-DMA, DLin-KC2-DMA, DODMA, PLGA, PEG, PEG-DMG, PEGylated lipids and amino alcohol lipids. In some aspects, the liposome comprises a cationic lipid such as, but not limited to, DLin-DMA, DLin-D-DMA, DLin-MC3-DMA, DLin-KC2-DMA, DODMA and amino alcohol lipids. The amino alcohol cationic lipid comprises in some aspects lipids described in and/or made by the methods described in U.S. Patent Publication No. US20130150625, herein incorporated by reference in its entirety. As a non-limiting example, the cationic lipid in certain aspects is 2-amino-3-[(9Z,12Z)-octadeca-9,12-dien-1-yloxy]-2-{[(9Z,2Z)-octadeca-9,12-dien-1-yloxy]methyl}propan-1-ol (Compound 1 in US20130150625); 2-amino-3-[(9Z)-octadec-9-en-1-yloxy]-2-{[(9Z)-octadec-9-en-1-yloxy]methyl}propan-1-ol (Compound 2 in US20130150625); 2-amino-3-[(9Z,12Z)-octadeca-9,12-dien-1-yloxy]-2-[(octyloxy)methyl]propan-1-ol (Compound 3 in US20130150625); and 2-(dimethylamino)-3-[(9Z,12Z)-octadeca-9,12-dien-1-yloxy]-2-{[(9Z, 12Z)-octadeca-9,12-dien-1-yloxy]methyl}propan-1-ol (Compound 4 in US20130150625); or any pharmaceutically acceptable salt or stereoisomer thereof.

In various embodiments, the liposome comprises (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319); (ii) a neutral lipid selected from DSPC, DPPC, POPC, DOPE and SM; (iii) a sterol, e.g., cholesterol; and (iv) a PEG-lipid, e.g., PEG-DMG or PEG-cDMA, in a molar ratio of about 20-60% cationic lipid:5-25% neutral lipid:25-55% sterol; 0.5-15% PEG-lipid.

In some embodiments, the liposome comprises from about 25% to about 75% on a molar basis of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), e.g., from about 35 to about 65%, from about 45 to about 65%, about 60%, about 57.5%, about 50% or about 40% on a molar basis.

In some embodiments, the liposome comprises from about 0.5% to about 15% on a molar basis of the neutral lipid e.g., from about 3 to about 12%, from about 5 to about 10% or about 15%, about 10%, or about 7.5% on a molar basis. Examples of neutral lipids include, but are not limited to, DSPC, POPC, DPPC, DOPE and SM. In some embodiments, the formulation includes from about 5% to about 50% on a molar basis of the sterol (e.g., about 15 to about 45%, about 20 to about 40%, about 40%, about 38.5%, about 35%, or about 31% on a molar basis. An exemplary sterol is cholesterol. In some embodiments, the formulation includes from about 0.5% to about 20% on a molar basis of the PEG or PEG-modified lipid (e.g., about 0.5 to about 10%, about 0.5 to about 5%, about 1.5%, about 0.5%, about 1.5%, about 3.5%, or about 5% on a molar basis. In some embodiments, the PEG or PEG modified lipid comprises a PEG molecule of an average molecular weight of 2,000 Da. In other embodiments, the PEG or PEG modified lipid comprises a PEG molecule of an average molecular weight of less than 2,000, for example around 1,500 Da, around 1,000 Da, or around 500 Da. Examples of PEG-modified lipids include, but are not limited to, PEG-distearoyl glycerol (PEG-DMG) (also referred herein as PEG-C14 or C14-PEG), PEG-cDMA (further discussed in Reyes et al. J. Controlled Release, 107, 276-287 (2005) the contents of which are herein incorporated by reference in their entirety)

In exemplary aspects, the cationic lipid may be selected from (20Z,23Z)—N,N-dimethylnonacosa-20,23-dien-10-amine, (17Z,20Z)—N,N-dimemylhexacosa-17,20-dien-9-amine, (1Z,19Z)—N,N-dimethylpentacosa-16, 19-dien-8-amine, (13Z,16Z)—N,N-dimethyldocosa-13,16-dien-5-amine, (12Z,15Z)—N,N-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimeihyloctacosa-19,22-dien-9-amine, (18Z,21 Z)—N,N-dimethylheptacosa-18,21-dien-8-amine, (17Z,20Z)—N,N-dimethylhexacosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21 Z,24Z)—N,N-dimethyltriaconta-21,24-dien-9-amine, (18Z)—N,N-dimetylheptacos-18-en-10-amine, (17Z)—N,N-dimethylhexacos-17-en-9-amine, (19Z,22Z)—N,N-dimethyloctacosa-19,22-dien-7-amine, N,N-dimethylheptacosan-10-amine, (20Z,23Z)—N-ethyl-N-methylnonacosa-20,23-dien-10-amine, 1-[(11Z,14Z)-1-nonylicosa-11,14-dien-1-yl]pyrrolidine, (20Z)—N,N-dimethylheptacos-20-en-10-amine, (15Z)—N,N-dimethyl eptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12,15-dien-1-amine, (13Z,16Z)—N,N-dimethyl-3-nonyldocosa-13,16-dien-1-amine, N,N-dimethyl-1-[(1S,2R)-2-octylcyclopropyl]eptadecan-8-amine, 1-[(1S,2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21-[(1S,2R)-2-octylcyclopropyl]henicosan-10-amine, N,N-dimethyl-1-[(1S,2S)-2-{[(1R,2R)-2-pentylcyclopropyl]methyl}cyclopropyl]nonadecan-10-amine, N,N-dimethyl-1-[(1S,2R)-2-octylcyclopropyl]hexadecan-8-amine, N,N-dimethyl-[(1R,2S)-2-undecylcyclopropyl]tetradecan-5-amine, N,N-dimethyl-3-{7-[(1S,2R)-2-octylcyclopropyl]heptyl}dodecan-1-amine, 1-[(1R,2S)-2-heptylcyclopropyl]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy)propan-2-amine, 1-{2-[(9Z,12Z)-octadeca-9,12-dien-1-yloxy]-1-[(octyloxy)methyl]ethyl}pyrrolidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy)methyl]ethyl}azetidine, (2S)-1-(hexyloxy)-N,N-dimethyl-3-[(9Z,12Z)-octadeca-9,12-dien-1-yloxy]propan-2-amine, (2S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy)propan-2-amine; (2S)—N,N-dimethyl-1-[(6Z,9Z,12Z)-octadeca-6,9,12-trien-1-yloxy]-3-(octyloxy)propan-2-amine, (2S)-1-[(11Z,14Z)-icosa-11,14-dien-1-yloxy]-N,N-dimethyl-3-(pentyloxy)propan-2-amine, (2S)-1-(hexyloxy)-3-[(11Z,14Z)-icosa-11,14-dien-1-yloxy]-N,N-dimethylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy)propan-2-amine, (2S)-1-[(13Z,16Z)-docosa-13,16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-metoyloctyl)oxyl-3-[(9Z,12Z)-octadeca-9,12-dien-1-yloxy]propan-2-amine, (2R)-1-[(3,7-dimethyloctyl)oxy]-N,N-dimethyl-3-[(9Z,12Z)-octadeca-9,12-dien-1-yloxy]propan-2-amine, N,N-dimethyl-1-(octyloxy)-3-({8-[(1S,2S)-2-{[(1R,2R)-2-pentylcyclopropyl]methyl}cyclopropyl]octyl}oxy)propan-2-amine, N,N-dimethyl-1-{[8-(2-oclylcyclopropyl)octyl]oxy}-3-(octyloxy)propan-2-amine and (11E,20Z,23Z)—N,N-dimethylnonacosa-11,20,2-trien-10-amine or a pharmaceutically acceptable salt or stereoisomer thereof.

In some embodiments, the composition comprises a lipid-polycation complex. The formation of the lipid-polycation complex may be accomplished by methods known in the art and/or as described in U.S. Pub. No. 20120178702, herein incorporated by reference in its entirety. As a non-limiting example, the polycation may include a cationic peptide or a polypeptide such as, but not limited to, polylysine, polyornithine and/or polyarginine. In some embodiments, the composition may comprise a lipid-polycation complex, which may further include a non-cationic lipid such as, but not limited to, cholesterol or dioleoyl phosphatidylethanolamine (DOPE).

Methods of Generating Liposomes

The present disclosure further provides methods of generating a liposome comprising ribonucleic acid (RNA) molecules and a cationic lipid, wherein the RNA molecules encode at least one MHC Class II epitope (and optionally at least one MHC Class I epitope) of a mutant Histone 3 (H3) protein comprising a K27M mutation and optionally at least one MHC Class I epitope of the mutant H3 protein.

In exemplary embodiments, the method comprises mixing any of the presently disclosed RNA molecules encoding at least one MHC Class II epitope (and optionally at least one MHC Class I epitope) of a mutant H3 protein comprising a K27M mutation (and optionally, at least one MHC Class I epitope) with a cationic lipid, including any one or more of those described herein. In various aspects, the method comprises mixing the RNA molecules and the cationic lipid at a RNA:cationic lipid ratio of about 1 to about 10 to about 1 to about 20, optionally, about 1 to about 15.

In exemplary embodiments, the method comprises producing the RNA molecules and then mixing the RNA molecules with the cationic lipid. In various instances, the RNA molecules are produced by in vitro transcription (IVT). Suitable techniques of carrying out IVT are known in the art. In exemplary aspects, an IVT kit is employed. In exemplary aspects, the kit comprises one or more IVT reaction reagents. As used herein, the term "in vitro transcription (IVT) reaction reagent" refers to any molecule, compound, factor, or salt, which functions in an IVT reaction. For example, the kit may comprise prokaryotic phage RNA polymerase and promoter (T7, T3, or SP6) with eukaryotic or prokaryotic extracts to synthesize proteins from exogenous DNA templates. In exemplary aspects, the kit is employed with a nucleic acid encoding the RNA molecule encoding the MHC Class II epitope (and optionally at least one MHC Class I epitope) of a mutant H3 protein comprising a K27M mutation and optionally the MHC Class I epitope of the mutant H3 protein. Optionally, the nucleic acid comprises the sequence of SEQ ID NO: 11. Accordingly, in exemplary aspects, the method comprises in vitro transcribing a nucleic acid comprising a nucleotide sequence encoding the RNA molecules encoding at least one MHC Class II epitope (and optionally at least one MHC Class I epitope) of a mutant H3 protein comprising a K27M mutation (and optionally at least one MHC Class I epitope) and mixing the RNA molecules with a cationic lipid. In various aspects, the nucleic acid comprises a sequence encoding a poly(A) tail so that the in vitro transcribed RNA molecule comprises a poly(A) tail at the 3' end. The method in various aspects, comprises additional processing steps, such as, for example, capping the in vitro transcribed RNA molecules. In exemplary instances, the method of generating a liposome comprising RNA molecules and a cationic lipid comprises (i) in vitro transcribing a nucleic acid comprising a nucleotide sequence encoding an RNA molecule encoding at least one MHC Class II epitope (and optionally at least one MHC Class I epitope) of a mutant H3 protein comprising a K27M mutation, (ii) chemically adding a 5'-cap to the in vitro transcribed RNA molecules, and (iii) mixing the RNA molecules comprising the 5'-cap with a cationic lipid. In various aspects, the method comprises mixing the RNA molecules and the cationic lipid at a RNA:cationic lipid ratio of about 1 to about 10 to about 1 to about 20, optionally, about 1 to about 15. With regard to the method, the cationic lipid may be any of those described herein. In various aspects, the cationic lipid is DOTAP. In various aspects, the RNA molecules and cationic lipid are mixed at a RNA:lipid ratio of about 1 to about 10 to about 1 to about 20. Optionally, the RNA molecules and cationic lipid are mixed at a RNA:lipid ratio of about 1 to about 15. In various aspects, the nucleotide sequence encoding the RNA molecules comprises the sequence of SEQ ID NO: 11. In various instances, the nucleotide sequence encoding the RNA molecules is operably linked to a promoter, optionally a T7 promoter. The nucleotide sequence encoding the RNA molecules is flanked by a 5' untranslated region (5'UTR) and a 3' untranslated region (3'UTR). In various aspects, the nucleic acid comprises a sequence encoding a polyA tail. In exemplary instances, the nucleic acid is a linearized plasmid.

In exemplary aspects, the method comprises downstream steps to prepare the liposomes for administration to a subject, e.g., a human. In exemplary instances, the method comprises formulating the lipid for intravenous injection. The method comprises in various aspects adding one or more pharmaceutically acceptable carriers, diluents, or excipients, and optionally comprises packaging the resulting composition in a container, e.g., a vial, a syringe, a bag, an ampoule, and the like. The container in some aspects is a ready-to-use container and optionally is for single-use.

The present disclosure also provides the liposome(s) generated by these presently disclosed methods. The liposome in some aspects may be formulated for intravenous injection.

Compositions

The present disclosure provides compositions relating to the presently disclosed nucleic acid molecules and liposomes. In exemplary embodiments, the composition comprises a liposome comprising ribonucleic acid (RNA) molecules and a cationic lipid, wherein the RNA molecules encode an MHC Class II epitope (and optionally at least one MHC Class I epitope) of a mutant Histone 3 (H3) protein comprising a K27M mutation. The compositions comprise any of the liposomes described herein. See, e.g., the section entitled Liposomes. For instance, the composition in exemplary aspects comprises a homogeneous population of a single type of liposome described herein. In alternative aspects, the composition comprises a heterogeneous mixture of liposomes that vary in size, zeta potential, amount of cationic lipid, amount of nucleic acid molecules, type of cationic lipid, and/or type of nucleic acid molecules. In exemplary aspects, the composition comprises about $10^{10}$ liposomes per mL to about $10^{15}$ liposomes per mL (e.g., about $10^{10}$ liposomes per mL, about $10^{11}$ liposomes per mL, about $10^{12}$ liposomes per mL, about $10^{13}$ liposomes per mL, about $10^{14}$ liposomes per mL. In some aspects, the composition comprises about $10^{12}$ liposomes±10% per mL. In exemplary aspects, the composition is administered in an amount based on the weight of the subject. In exemplary aspects, about 1 to about 10 μL (e.g., about 2 to about 7 μL, about 2, 3, 4, 5, 6, or 7 μL, about 2.5 μL) of a solution comprising about $10^{12}$ liposomes per mL is administered per kg body weight.

In various aspects, the compositions of the present disclosure comprises components in addition to the liposome, nucleic acid molecule encoding the MHC Class II epitope (and optionally at least one MHC Class I epitope) and/or nucleic acid molecule comprising a sequence encoding the nucleic acid molecule encoding the MHC Class II epitope (and optionally at least one MHC Class I epitope). In some aspects, the compositions further comprise a pharmaceutically acceptable carrier, excipient or diluent. In exemplary aspects, the composition is a pharmaceutical composition intended for administration to a human. In exemplary aspects, the composition is a sterile composition. The composition, in various aspects, comprises any pharmaceutically acceptable ingredient, including, for example, acidifying agents, additives, adsorbents, aerosol propellants, air displacement agents, alkalizing agents, anticaking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, water-miscible cosolvents, water softeners, or wetting agents. See, e.g., the *Handbook of Pharmaceutical Excipients*, Third Edition, A. H. Kibbe (Pharmaceutical Press, London, U K, 2000), which is incorporated by reference in its entirety. *Remington's Pharmaceutical Sciences*, Sixteenth Edition, E. W. Martin (Mack Publishing Co., Easton, Pa., 1980), which is incorporated by reference in its entirety.

The composition of the present disclosure can be suitable for administration by any acceptable route, including parenteral and subcutaneous. Other routes include intravenous, intradermal, intramuscular, intraperitoneal, intranodal and intrasplenic, for example. In exemplary aspects, when the composition comprises the liposomes (not cells comprising the liposomes), the composition is suitable for systemic (e.g., intravenous) administration. In exemplary aspects, when the composition comprises cells comprising the liposomes (and not liposomes outside of cells), the composition is suitable for intradermal administration. In exemplary aspects, the composition is systemically administered via parenteral administration. In exemplary aspects, the composition is administered via injection or infusion. In exemplary instances, the composition is administered subcutaneously or intravenously or intramuscularly. In some aspects, the composition is administered intravenously.

If the composition is in a form intended for administration to a subject, it can be made to be isotonic with the intended site of administration. For example, if the solution is in a form intended for administration parenterally, it can be isotonic with blood. The composition typically is sterile. In certain embodiments, this may be accomplished by filtration through sterile filtration membranes. In certain embodiments, parenteral compositions generally are placed into a container having a sterile access port, for example, an intravenous solution bag, or vial having a stopper pierceable by a hypodermic injection needle, or a prefilled syringe. In certain embodiments, the composition may be stored either in a ready-to-use form or in a form (e.g., lyophilized) that is reconstituted or diluted prior to administration.

In some embodiments, the composition of the present disclosure can be formulated for controlled release and/or targeted delivery. As used herein, "controlled release" refers to a pharmaceutical composition or compound release profile that conforms to a particular pattern of release to effect a therapeutic outcome. In some embodiments, the liposome composition may be encapsulated into a delivery agent described herein and/or known in the art for controlled release and/or targeted delivery. As used herein, the term "encapsulate" means to enclose, surround or encase. As it relates to the formulation of the compounds of the disclosure, encapsulation may be substantial, complete or partial. The term "substantially encapsulated" means that at least greater than 50, 60, 70, 80, 85, 90, 95, 96, 97, 98, 99, 99.9, 99.9 or greater than 99.999% of the pharmaceutical composition or compound of the disclosure may be enclosed, surrounded or encased within the delivery agent. "Partially encapsulation" means that less than 10, 10, 20, 30, 40 50 or less of the pharmaceutical composition or compound of the disclosure may be enclosed, surrounded or encased within the delivery agent. Advantageously, encapsulation may be determined by measuring the escape or the activity of the pharmaceutical composition or compound of the disclosure using fluorescence and/or electron micrograph. For example, at least 1, 5, 10, 20, 30, 40, 50, 60, 70, 80, 85, 90, 95, 96, 97, 98, 99, 99.9, 99.99 or greater than 99.99% of the pharmaceutical composition or compound of the disclosure are encapsulated in the delivery agent.

Methods of Use

Without being bound to any particular theory, the data provided herein for the first time support the use of the liposomes comprising RNA molecules and a cationic lipid, wherein the RNA molecules encode an MHC Class II epitope (and optionally at least one MHC Class I epitope) of a mutant Histone 3 (H3) protein comprising a K27M mutation, in methods of increasing in a subject the level or number of central memory T cells. In various aspects, the liposomes are particularly useful for increasing in a subject the level or number of central memory T cells having antigen specificity for an epitope of a mutant Histone 3 (H3) protein comprising a K27M mutation. In various aspects, the liposomes are particularly useful for increasing in a subject the level or number of central memory T cells which activate the immune system against tumor cells, e.g., cells of a diffuse midline glioma (DMG). Accordingly, the present disclosure provides methods of increasing in a subject the number of central memory T cells having antigen specificity for an epitope of a mutant Histone 3 (H3) protein comprising a K27M mutation. In exemplary aspects, the method comprises administering to the subject a liposome comprising RNA molecules and a cationic lipid, wherein the RNA molecules encode an MHC Class II epitope (and optionally at least one MHC Class I epitope) of a mutant Histone 3 (H3) protein comprising a K27M mutation, or a composition comprising the same, in an amount effective to increase the central memory T cells in the subject. The present disclosure also provides methods of enhancing in a subject an immune response against tumor cells, e.g., cells of a DMG, expressing a mutant Histone 3 (H3) protein comprising a K27M mutation. In exemplary aspects, the method comprises administering to the subject a liposome comprising RNA molecules and a cationic lipid, wherein the RNA molecules encode an MHC Class II epitope (and optionally at least one MHC Class I epitope) of a mutant Histone 3 (H3) protein comprising a K27M mutation, or a composition comprising the same, in an amount effective to increase the an immune response against the DMG in the subject. In exemplary aspects, the subject has a diffuse midline glioma (DMG) expressing a mutant Histone 3 (H3) protein comprising a K27M mutation or a predisposition to having the DMG. The subject in various instances has been treated for a DMG or is in remission for the DMG. Optionally, the method further comprises administering to the subject one or more lysosome-associated membrane proteins (LAMPs).

As used herein, the term "increase" and "enhance" and words stemming therefrom may not be a 100% or complete increase or enhancement. Rather, there are varying degrees of increasing or enhancing of which one of ordinary skill in the art recognizes as having a potential benefit or therapeutic effect. The presently disclosed methods may for instance delay the onset or re-occurrence/relapse of the disease or a symptom thereof to any amount or level. In exemplary embodiments, the increase or enhancement provided by the methods is at least or about a 10% increase or enhancement (e.g., at least or about a 20% increase or enhancement, at least or about a 30% increase or enhancement, at least or about a 40% increase or enhancement, at least or about a 50% increase or enhancement, at least or about a 60% increase or enhancement, at least or about a 70% increase or enhancement, at least or about a 80% increase or enhancement, at least or about a 90% increase or enhancement, at least or about a 95% increase or enhancement, at least or about a 98% increase or enhancement).

Methods of treating a subject with a diffuse midline glioma (DMG) expressing a mutant Histone 3 (H3) protein comprising a K27M mutation are furthermore provided herein. In exemplary aspects, the method comprises administering to the subject a liposome comprising RNA molecules and a cationic lipid, wherein the RNA molecules encode an MHC Class II epitope (and optionally at least one MHC Class I epitope) of a mutant Histone 3 (H3) protein comprising a K27M mutation, or a composition comprising the same, in an amount effective to treat the DMG in the subject.

As used herein, the term "treat," as well as words related thereto, do not necessarily imply 100% or complete treatment. Rather, there are varying degrees of treatment of which one of ordinary skill in the art recognizes as having a potential benefit or therapeutic effect. In this respect, the methods of treating a disease of the present disclosure can provide any amount or any level of treatment. Furthermore, the treatment provided by the method may include treatment of one or more conditions or symptoms or signs of the disease being treated. For instance, the treatment method of the presently disclosure may inhibit one or more symptoms of the disease. Also, the treatment provided by the methods of the present disclosure may encompass slowing the progression of the disease. The term "treat" also encompasses prophylactic treatment of the disease. Accordingly, the treatment provided by the presently disclosed method may delay the onset or reoccurrence/relapse of the disease being prophylactically treated. In exemplary aspects, the method delays the onset of the disease by 1 day, 2 days, 4 days, 6 days, 8 days, 10 days, 15 days, 30 days, two months, 4 months, 6 months, 1 year, 2 years, 4 years, or more. The prophylactic treatment encompasses reducing the risk of the disease being treated. In exemplary aspects, the method reduces the risk of the disease 2-fold, 5-fold, 10-fold, 20-fold, 50-fold, 100-fold, or more.

In certain aspects, the method of treating the disease may be regarded as a method of inhibiting the disease, or a symptom thereof. As used herein, the term "inhibit" and words stemming therefrom may not be a 100% or complete inhibition or abrogation. Rather, there are varying degrees of inhibition of which one of ordinary skill in the art recognizes as having a potential benefit or therapeutic effect. The presently disclosed methods may inhibit the onset or re-occurrence of the disease or a symptom thereof to any amount or level. In exemplary embodiments, the inhibition provided by the methods is at least or about a 10% inhibition (e.g., at least or about a 20% inhibition, at least or about a 30% inhibition, at least or about a 40% inhibition, at least or about a 50% inhibition, at least or about a 60% inhibition, at least or about a 70% inhibition, at least or about a 80% inhibition, at least or about a 90% inhibition, at least or about a 95% inhibition, at least or about a 98% inhibition).

With regard to the foregoing methods, the liposomes or the composition comprising the same in some aspects is systemically administered to the subject. Optionally, the method comprises administration of the liposomes or composition by way of parenteral administration. In various instances, the liposome or composition is administered to the subject intravenously.

In various aspects, the liposome or composition is administered according to any regimen including, for example, daily (1 time per day, 2 times per day, 3 times per day, 4 times per day, 5 times per day, 6 times per day), three times a week, twice a week, every two days, every three days, every four days, every five days, every six days, weekly, bi-weekly, every three weeks, monthly, or bi-monthly. In various aspects, the liposomes or composition is/are administered to the subject once a week.

Subjects

The subject is a mammal, including, but not limited to, mammals of the order Rodentia, such as mice and hamsters, and mammals of the order Logomorpha, such as rabbits, mammals from the order Carnivora, including Felines (cats) and Canines (dogs), mammals from the order Artiodactyla, including Bovines (cows) and Swines (pigs) or of the order Perssodactyla, including Equines (horses). In some aspects, the mammals are of the order Primates, Ceboids, or Simoids (monkeys) or of the order Anthropoids (humans and apes). In some aspects, the mammal is a human. In some aspects, the human is an adult aged 18 years or older. In some aspects, the human is a child aged 17 years or less. In exemplary aspects, the subject has a DMG. In various instances, the DMG is diffuse intrinsic pontine glioma (DIPG).

The following examples are given merely to illustrate the present invention and not in any way to limit its scope.

EXAMPLES

Example 1

This example describes a method of generating a liposome of the present disclosure.

An MHC Class II epitope of a mutant Histone 3 (H3) protein comprising a K27M mutation was selected by using the NetMHCII2.3a and NetMHCcons1.1 prediction servers to predict potential MHC-restricted epitopes present within a peptide sequence encompassing the K27M mutation of the mutant H3 protein. For a given input amino acid sequence, the netMHCII2.3a server predicts the MHC Class II binding site(s) across multiple mouse and human MHCII alleles within a sequence of up to 15 amino acids of the input sequence (query sequence). The alleles included a range of human HLA Class II subtypes including HLA-DR (7/25), HLA-DPA (2/9), HLA-DQA (10/20), and HLA-A and B* (10/12). The current algorithm is available at the IP address "http://" followed by "www.cbs.dtu.dk/services/NetMHCII/". FIG. 1 shows the mutant 26-mer (25-mer including start codon) query sequence chopped up into 15-mer segments for prediction and the affinity and % rank for each 15-mer segment. The table at the bottom of FIG. 1 lists amino acid sequences reflecting the range of 15-mers that possess weak to strong binding. Potential strong binders are displayed as having a % rank <5.0. As you can see from FIG. 1, the sequence RKQLATKAARMSAPSTGGVKKP (SEQ ID NO: 22) contained 15-mers with a % rank of less than 5.0. A sequence comprising SEQ ID NO: 22 (H3 Mut 26-mer) was identified through this analysis.

The above-described in silico analysis was also performed on an input wild-type (WT) H3 sequence lacking the K27M mutation. Through this analysis, a correlative WT 26-mer sequence comprising predicted MHC Class II strong binding epitopes was identified.

DNA template molecules encoding a H3 Mut 26-mer or the version lacking the K27M mutation (H3 WT 26-mer), or encoding full length versions of the mutant H3 protein (H3 Mut FL) or WT H3 protein (H3 WT FL) were synthesized. Each DNA template molecule was engineered into a plasmid comprising a T7 promoter, 5'- and 3'-UTRs flanking the DNA template molecules (coding sequence), and a sequence encoding a poly(A) tail. A visual of the sequence design of the plasmid is shown in FIG. 2. Plasmids comprising the different DNA template molecules were amplified, extracted, then linearized and purified. The linearized, purified plasmids were then used as templates for RNA production via in vitro transcription (IVT). IVT was carried out using the mMESSAGE mMACHINE™ T7 transcription kit (ThermoFisher Scientific, Catalog number AM1344). The resulting RNA molecules comprising a poly(A) tail were used in a chemical capping reaction to add a cap at the 5' end of the RNA molecule. These capped RNA molecules were subsequently used to assemble RNA nanoparticles (NP) or liposomes.

FIG. 2 provides an exemplary schematic of the steps that result in the generation of RNA NPs. Nanoparticles (NPs), also referred to herein as liposomes, may be generated by any means known in the art, including but not limited to the methods described in Sayour et al., *Oncoimmunology* 2016, e1256527. In Sayour et al., 2016, supra, it is taught that the cationic lipid DOTAP (powder form) is acquired from Avanti, Polar Lipids Inc. (Alabaster, AL, USA). For preparation, chloroform is added to re-suspend 25-100 mg; chloroform is evaporated off until a thin lipid layer remains. The mixture is re-suspended in 5-20 mL of PBS before being placed in 50° C. water bath for 1-2 hours with intermittent vortexing. Within twenty-four hours, PBS (5-20 mL) is added to the mixture, vortexed and placed in a bath sonicator for 5 minutes before passage through a 0.43 μm and a 0.22 μm syringe filter (PALL Acrodisc syringe filter with Supor membrane). The final NP solution (2.5 μg/uL) is based on pre-filtration DOTAP concentration (2.5 μg/μL).

For in vivo studies: 25 μg of RNA is added to 375 μg of DOTAP (per mouse) in PBS buffer. For in vitro studies: 1.67 μg of RNA is added to 25 μg of DOTAP (per $1\times10^5$ cells) in PBS buffer. In both cases, the mixture is kept at room temperature (~15-20 minutes) to facilitate complex formation.

Example 2

This example describes an in vivo method of administering the liposomes to evaluate the immunogenicity of the liposomes designed to target the mutant H3 protein comprising the K2M mutation.

The purpose of this study was to show that H3.3 K27M neoantigens can drive a immunotherapeutic response against DIPG via RNA-NPs (liposomes). Neoantigen targeted RNA-NPs were formulated and examined for their immunogenicity using CD4+ and CD8+ T cell proliferation and cytotoxicity assays.

Figure 3A:
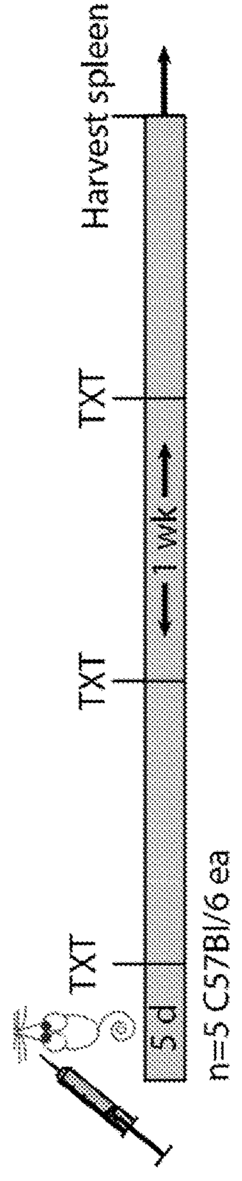
FIG. 3A is a schematic of a process of administering a composition of the present disclosure.

C57BL/6 mice, and Tdtomato reporter A14 mice and OT-I transgenic mice on the C57BL/6 background were purchased from Jackson Laboratories. Animal procedures were approved by the University of Florida Institutional Animal Care and Use Committee. Mice (n=5) were treated with (A) RNA-NPs comprising capped RNA molecules encoding a H3 Mut 26-mer described in Example 1 (H3mer RNA-NP), (B) NPs comprising ovalbumin RNA (OVA RNA-NP or OVA-NP) which served as a positive control, or (C) NPs without any RNA (a negative control; NP alone). Nanoparticles (200 μL) were injected into the tail vein of C57Bl/6 mice. Mice were treated once a week for 3 weeks. Mice were sacrificed one week following the last treatment and spleens were harvested. A schematic of the treatment protocol is shown in FIG. 3A.

Figure 3B:
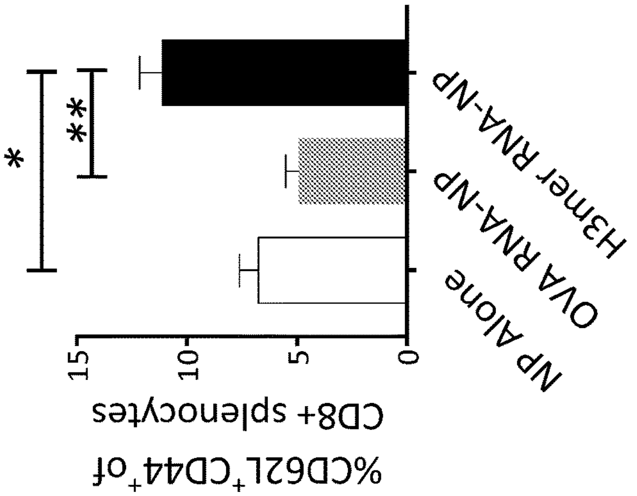
FIG. 3B is a graph of the % of $CD62L^+CD44^+$ cells of $CD8^+$ splenocytes obtained from mice treated with nanoparticles alone (NP alone), nanoparticles complexed with ovalbumin RNA (OVA RNA-NP) or nanoparticles complexed with RNA encoding MHC Class II epitopes of a mutant Histone3 (H3) protein comprising a K27M mutation (H3mer RNA-NP). This demonstrates expansion of the central memory population of T cells which play a key role in maintaining long-term antigen-specific immunogenicity to their respective target which may ultimately allow long-term anti-tumor immunity.
Figure 3C:
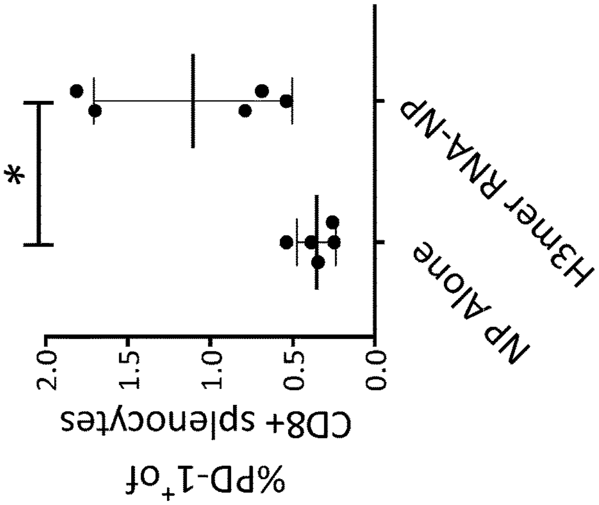
FIG. 3C is a graph of the % of $PD\text{-}1^+$ cells of $CD8^+$ splenocytes obtained from mice treated with nanoparticles alone (NP alone) or nanoparticles complexed with RNA encoding an MHC Class II epitope of a mutant Histone3 (H3) protein comprising a K27M mutation (H3mer RNA-NP). Transient PD-1 expression is indicative of TCR-mediated activation of T cells and reinforce the encoded peptide's capacity to induce an antigen-specific lymphocyte population.

Splenocytes of the harvested spleens were phenotypically analyzed by flow cytometry. As shown in FIG. 3B, the % of CD62L+CD44+ cells of CD8+ splenocytes were increased in the spleens of mice treated with H3mer RNA-NP, compared to controls, suggesting that the central memory phenotype in H3mer-NP administered mice was increased. The % of PD-1+ cells of CD8+ splenocytes were also measured. As shown in FIG. 3C, mice treated with H3mer RNA-NP exhibited an elevated expression of PD-1 in CD8+ T cells, suggesting that T cell activation was induced. These data demonstrate that mice treated with H3-mer RNA NPs increased activated central memory T cells.

Figure 4A:
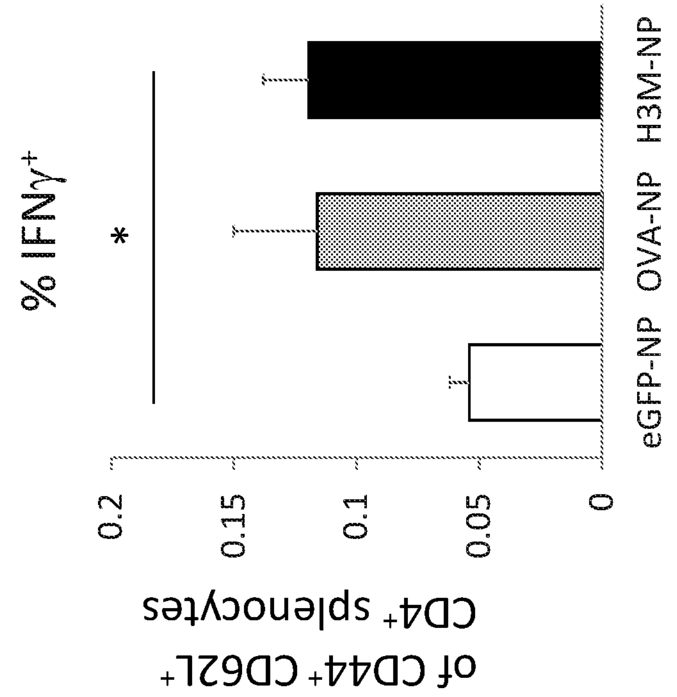
FIG. 4A is a graph of the % of IFNγ expressing cells of CD44+CD62L+CD4+ splenocytes in mice administered an NP encapsulated-irrelevant RNA (eGFP), immunostimulatory –OVA encoding RNA, and the H3 mutant oligomer encoding RNA once a week for 3 weeks. Splenocytes were harvested one week after the final injection. Since IFNγ release by central memory is driven by antigen recognition, these findings support the production of an antigen specific central memory compartment in H3M-NP administered mice.
Figure 4B:
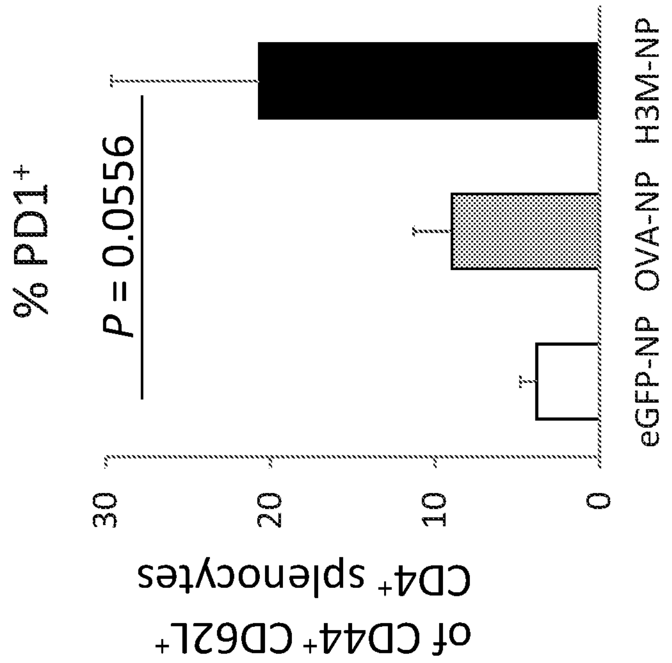
FIG. 4B is a graph of the % of PD-1 expressing cells of CD44+CD62L+CD4+ splenocytes. The potentiated expression of PD-1 in H3M-NP treated mice relative to the irrelevant-RNA encoding control recapitulates and supports the findings presented in 3C.

The expression of IFNγ and PD1+ by CD44+CD62L+ cells of the CD4+ subset of splenocytes harvested from mice was measured by flow cytometry. As shown in FIG. 4A, IFNγ expression of CD44+CD62L+ cells of the CD4+ subset of splenocytes was increased in the spleens of H3M-NP treated mice. PD1 expression by these cells was likewise increased (FIG. 4B). These data suggest that CD4 memory cell expression of IFNγ and PD1 is elevated in mice treated with the H3mer-RNA NPs.

The above results are consistent with previous observations made in separate experiments.

In a first separate experiment, mouse models expressing highly immunogenic OVA peptide were injected with OVA-RNA NPs, NP alone, or untreated. In this experiment, OVA-RNA NPs represent NPs comprising RNA molecules encoding MHC Class I-restricted epitopes of a tumor antigen. The % of mice surviving for the indicated number of days post tumor implantation were observed and recorded. As shown in FIG. 5A, the % survival past 30 days post tumor implantation was increased in mice treated with OVA-RNA NPs, compared to untreated mice and mice treated with NP alone (without RNA).

In another separate experiment, mouse models of another type were injected with NPs complexed with total tumor RNA (tumor mRNA-NP) or left untreated. In this experiment, tumor mRNA NPs represent NPs comprising RNA molecules encoding MHC Class I- and MHC Class II epitopes of a tumor antigen. The % of mice surviving for the indicated number of days post tumor implantation were observed and recorded. As shown in FIG. 5B, the mice treated with total tumor RNA NPs survived beyond 100 days, whereas untreated mice did not survive past 40 days.

Taken together these data suggest the importance of NPs comprising RNA molecules encoding both Class I and Class II-restricted epitopes.

In previous studies, it was shown that the % of antigen specific CD8+ spenocytes of RNA-NP treated mice was increased compared to control mice treated with RNA alone, NPs complexed with control RNA, or untreated. Also, our previous work shows that the such cells demonstrated higher IFNγ expression, which confirms the generation of antigen-specific immunogenicity. These data support that antigen specific CD8+ cells are activated upon treatment with NPs complexed with tumor relevant RNA molecules. FIG. 5C. A similar effect was observed in a separate experiment wherein mice were treated with NPs complexed with total tumor RNA (TTmRNA-NP). Mice treated with TTmRNA-NP displayed a higher percentage of CD11c+CD86+ cells and also a higher percentage of CD62L+CD44+CD3+ cells, relative to untreated mice and mice treated with Green Fluorescence Protein (GFP) RNA complexed NPs (FIGS. 5D and 5E). The observations shown in FIGS. 5A-5E collectively support that Class I restricted RNA epitopes do not mediate survivor benefits but total tumor RNA antigens mediate substantial survivorship.

This example demonstrates the importance of MHC Class II epitopes of a mutant H3 protein.

Example 3

This example describes a method of using LAMP vaccine in combination with the NPs of Example 1.

RNA molecules encoding a chimeric protein comprising LAMP and the MHC Class II epitope of the mutant H3 protein comprising the K27M mutation are made by in vitro translation as essentially described in Example 1. These RNA molecules are complexed with nanoparticles (liposomes). The formulated nanoparticles are then injected into the tail vein of mice as essentially described in Example 2. CTL assays using the splenocytes from harvested spleens are carried out as described in Example 2, as well as the measurements of % effector memory, % central memory and % PD-1 expressing cells.

Also, we will assay for enhanced MHC II presentation in LAMP and DC-LAMP conjugated templates. Tumor bearing, eYFP reporting IFNγ, "GREAT," mice will be administered 1) NPs alone, or: 2) neoantigen, 3) LAMP/neoantigen, 4) DC-LAMP/neoantigen, 5) equimolar LAMP and DC-LAMP/neoantigen RNA-NPs (n=10 per group; see Aim 1 admin.). DIPG cell line with hallmark mutations is courtesy Oren Becher, MD, at Northwestern. One week later we will harvest spleens and tumors for tetramer, Th1/Th2, DC, and T cell flow cytometry. If LAMPs enhance MHC II presentation, we anticipate increased CD4+ and CD8+ T cell recruitment as well as elevated $IFN\gamma^{+}$ and $tetramer^{+}$ cells Without being bound to a particular theory, the inclusion of the RNA encoding the LAMP leverages a trafficking signal which guides the antigen (H3K27M) to the lysosomes in antigen presenting cells. It is compelled to enter a pathway that results in the presentation of the antigen to CD4+ cells, often referred to as "helper T cells". CD4+ T cells are involved in affecting many aspects of a complex immune response: cytokine release, immunological memory, antibody production, and support for other T cell types. It is also believed that the inclusion of LAMP RNA will drive the orientation of the CD4+ T cell to a particular sub-type, the Th1 T cell. Th1 cells produce inflammatory and immunity inducing chemical messengers, cytokines, that can help stimulate the immune response. This approach is also believed to induce a broad immune response and thereby results in enhanced CD8+ T cell responses as well.

Example 4

This example demonstrates the immunologic targeting of DIPG with H3K27M encoding RNA-nanoparticles.

Background: DIPG remains uniformly recalcitrant and necessities development of novel targeted therapies. The histone mutation in H3K27M is conserved in the preponderance of DIPG patients and may be exploited as a neoepitope for cancer immunotherapy. We have developed a novel treatment platform, which leverages the use of clinically translatable nanoparticles (NPs) combined with H3K27M mRNA neoantigens for in vivo activation of dendritic cells and generation of DIPG specific T cells.

Objective: Since neoantigens have been shown to mediate immunologic response through MHC class II, we sought to identify MHCII restricted epitopes spanning the H3K27M junction for development of RNA-NP vaccines against DIPG Results: We identified a MHC Class II-restricted H3K27M epitope that was not present in the wild-type sequence. We constructed a 25-mer sequence (75 amino acids) spanning this range, before cloning it into our custom pGEM-4z plasmid containing a poly A tail and 5' UTR with a T7 promoter for amplification of MHC-II restricted H3K27M mRNA. We complexed this RNA with our custom NP formulation and investigated its immunogenicity in C57Bl/6 mice. Unlike MHC-I restricted epitopes (i.e. OVAlbumin's SINFEKL epitope) MHC-II restricted H3K27M epitopes elicited significant increases in activated CD4 and CD8 central memory T cells. We demonstrate that this central memory phenotype correlates with anti-tumor efficacy and long-term survival outcomes in murine tumor models.

Conclusion: RNA-NPs can be made readily available for all DIPG patients (and not only HLA specific haplotypes) providing a renewable antigen resource that can be used to continuously vaccinate patients for months/years after diagnosis. Herein, we identify MHCII restricted K27M epitopes for activation of immunologic central memory necessary for long-lived anti-tumor efficacy.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed:

1. A composition comprising a liposome comprising ribonucleic acid (RNA) molecules and a cationic lipid, wherein the RNA molecules encode at least one MHC Class II epitope (i) comprising at least 30 amino acids of a mutant Histone 3 (H3) protein comprising a K27M mutation and (ii) comprising the amino acid sequence of MAPRKQLATKAARMSAPSTGGVKKPH (SEQ ID NO: 13) or RKQLATKAARMSAPSTGGVKK (SEQ ID NO: 15), wherein the liposome has a zeta potential of about 30 mV to about 60 mV.

2. The composition of claim 1, wherein at least a portion of the RNA molecules comprise the nucleotide sequence of SEQ ID NO: 12.

3. The composition of claim 1, wherein the RNA molecules encode at least 2 MHC Class II epitope of the mutant H3 protein.

4. The composition of claim 1, wherein the RNA molecules encode a peptide that binds to at least one or more human MHC Class II molecules.

5. The composition of claim 1, wherein the liposome comprises RNA molecules that encode at least one MHC Class I epitope of the mutant H3 protein.

6. The composition of claim 1, wherein the RNA molecules encode a peptide that binds to at least one or more human MHC Class I molecules.

7. The composition of claim 1, wherein the cationic liposome is 1,2-dioleoyl-3-trimethylammonium-propane (DOTAP).

8. The composition of claim 1, wherein the composition comprises a plurality of liposomes, each liposome of which is about 50 nm to about 250 nm in diameter.

9. The composition of claim 1, wherein the RNA molecules are complexed with the cationic lipid via electrostatic interactions.

10. The composition of claim 1, wherein the RNA molecules comprise a 5'-cap.

11. The composition of claim 1, wherein the RNA molecules further encode a lysosome-associated membrane protein (LAMP).

12. A method of generating a liposome comprising ribonucleic acid (RNA) molecules and a cationic lipid, wherein the RNA molecules encode at least one MHC Class II epitope of a mutant Histone 3 (H3) protein comprising a K27M mutation, said method comprising (i) in vitro transcribing a nucleic acid comprising a nucleotide sequence encoding the RNA molecules, (ii) chemically adding a 5'-cap to the in vitro transcribed RNA molecules, and (iii) mixing the RNA molecules comprising the 5'-cap with a cationic lipid, wherein the liposome has a zeta potential of about 30 mV to about 60 mV.

13. A liposome generated by the method of claim 12.

14. A composition comprising the liposome of claim 13.

15. A method of increasing in a subject the number of central memory T cells having antigen specificity for an epitope of a mutant Histone 3 (H3) protein comprising a K27M mutation, said method comprising administering to the subject a composition of claim 1 in an amount effective to increase the central memory T cells in the subject.

16. A method of enhancing in a subject an immune response against a diffuse midline glioma (DMG) expressing a mutant Histone 3 (H3) protein comprising a K27M mutation, said method comprising administering to the subject a composition of claim 1 in an amount effective to increase an immune response against the DMG in the subject.

17. A method of treating a subject with a diffuse midline glioma (DMG) expressing a mutant Histone 3 (H3) protein comprising a K27M mutation, said method comprising administering to the subject a composition of claim 1, in an amount effective to treat the DMG in the subject.

18. The composition of claim 1, wherein the RNA molecules encode SEQ ID NO: 1.

* * * * *